US006248549B1

(12) United States Patent
Van Eyk et al.

(10) Patent No.: US 6,248,549 B1
(45) Date of Patent: Jun. 19, 2001

(54) METHODS OF MODULATING MUSCLE CONTRACTION

(75) Inventors: Jennifer E. Van Eyk; Alan S. Mak; Graham P. Côté, all of Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/100,930

(22) Filed: Jun. 22, 1998

Related U.S. Application Data

(60) Provisional application No. 60/089,505, filed on Jun. 16, 1998, and provisional application No. 60/050,478, filed on Jun. 23, 1997.

(51) Int. Cl.$^7$ ................................ C12Q 1/48; C12N 9/12
(52) U.S. Cl. ............................................. 435/15; 435/194
(58) Field of Search ..................... 435/15, 194; 424/906, 424/94.1; 530/841

(56) References Cited

U.S. PATENT DOCUMENTS

| 4,925,649 | * | 5/1990 | Counsell et al. ................. 424/1.1 |
| 5,443,962 | * | 8/1995 | Draetta et al. ................... 435/29 |
| 5,605,825 |   | 2/1997 | Abo et al. ....................... 435/194 |
| 5,906,819 | * | 5/1999 | Kaibuchi et al. ................ 424/94.5 |

OTHER PUBLICATIONS

Lim et al., "Regulation f phosphorylation pathways by p21 GTPases The p21 Ras–related Rho Subfamily and its role in phosphorylation signalling pathways", Eur. J. Biochem. vol. 242, Feb. 1996, pp. 171–185.*

Bagrodia, S., et al., "Identification of a mouse p21$^{Cdc42/Rac}$ activated kinase", J. Biol. Chem. 270: 22731–22737 (1995).

Clerk, A., et al., "Activation of p21–activated protein kinase α (αPAK) by hyperosmotic shock in neonatal ventricular myocytes", FEBS Letters 403: 23–25 (1997).

Joneson, T. et al., "RAC regulation of actin polymerization and proliferation by a pathway distinct from Jun kinase", Science 274: 1374–1376 (Nov. 1996).

Karibe, H., et al., "Inhibitory effects of protein kinase inhibitors and cytoskeletal inhibitors on Ca$^{2+}$–free contraction of rat uterus", European J. Pharmacol. 188: 407–410 (1990).

Kureishi, Y., et al., "Rho–associated kinase directly induces smooth muscle contraction through myosin light chain phosphorylation", J. Biol. Chem. 272: 12257–12260 (May 1997).

Lian, J.P., et al., "Activation of the p21–activated protein kinases from neutrophils with an antibody that reacts with the N–terminal region of Pak 1", FEBS Letters 404: 211–215 (1997).

Manser, E., et al., "Expression of constitutively active α–PAK reveals effects of the kinase on actin and focal complexes", Mol. Cell. Biol. 17: 1129–1143 (Mar. 1997).

Sells, M.A., et al., "Human p21–activated kinase (Pak1) regulates actin organization in mammalian cells", Curr. Biol. 7: 202–210 (Feb. 1997).

Tsakiridis, T., et al., "Insulin activates a p21–activated kinase in muscle cells via phosphatidylinositol 3–kinase", J. Biol. Chem. 271: 19664–19667 (Aug. 1996).

Tuazon, P.T., et al., "Phosphorylation of myosin light chain by a protease–activated kinase from rabbit skeletal muscle", Eur. J. Biochem. 129: 205–209 (1982).

Tuazon, P.T., et al., "Activation of actin–activated ATPase in smooth muscle by phosphorylation of myosin light chain with protease–activated kinase I", J. Biol. Chem. 259: 541–546 (Jan. 1984).

Zhang, S., et al., "Rho family GTPases regulate p38 mitogen–activated protein kinase through the downstream mediator Pak1", J. Biol. Chem. 270: 23934–23936 (Oct. 1995).

Winder et al. Calponin phosphorylation in vitro and in intact muscle. Biochemical Journal, 296 (3), pp. 827–836, (Dec. 1993).*

* cited by examiner

Primary Examiner—Ardin H. Marschel
Assistant Examiner—Marjorie A. Moran
(74) Attorney, Agent, or Firm—Carol Miernicki Steeg; Stephen J. Scribner; Maria Laccotripe Zacharakis

(57) ABSTRACT

Methods of modulating calcium independent smooth muscle contraction, and of modulating cardiac muscle contraction, by the administration of a PAK modulating agent are described. A method of treating a subject having a state characterized by smooth muscle contraction, (e.g., hypertension, asthma, irritable bowel syndrome, incontinence and menstrual cramps) or cardiac contractile dysfunction (e.g., heart failure and myocardial stunning) is also described. The method involves the administration, to a subject, of a therapeutically effective amount of a PAK modulating agent, e.g., a PAK inhibitor or stimulator. Assays, e.g., screening tests, to identify PAK modulating agents or agents that modulate muscle contraction are also provided.

8 Claims, 20 Drawing Sheets

1. pCa 8.3
2. pCa 8.3, + PAK
3. pCa 8.3, + ROK
4. pCa 4.3

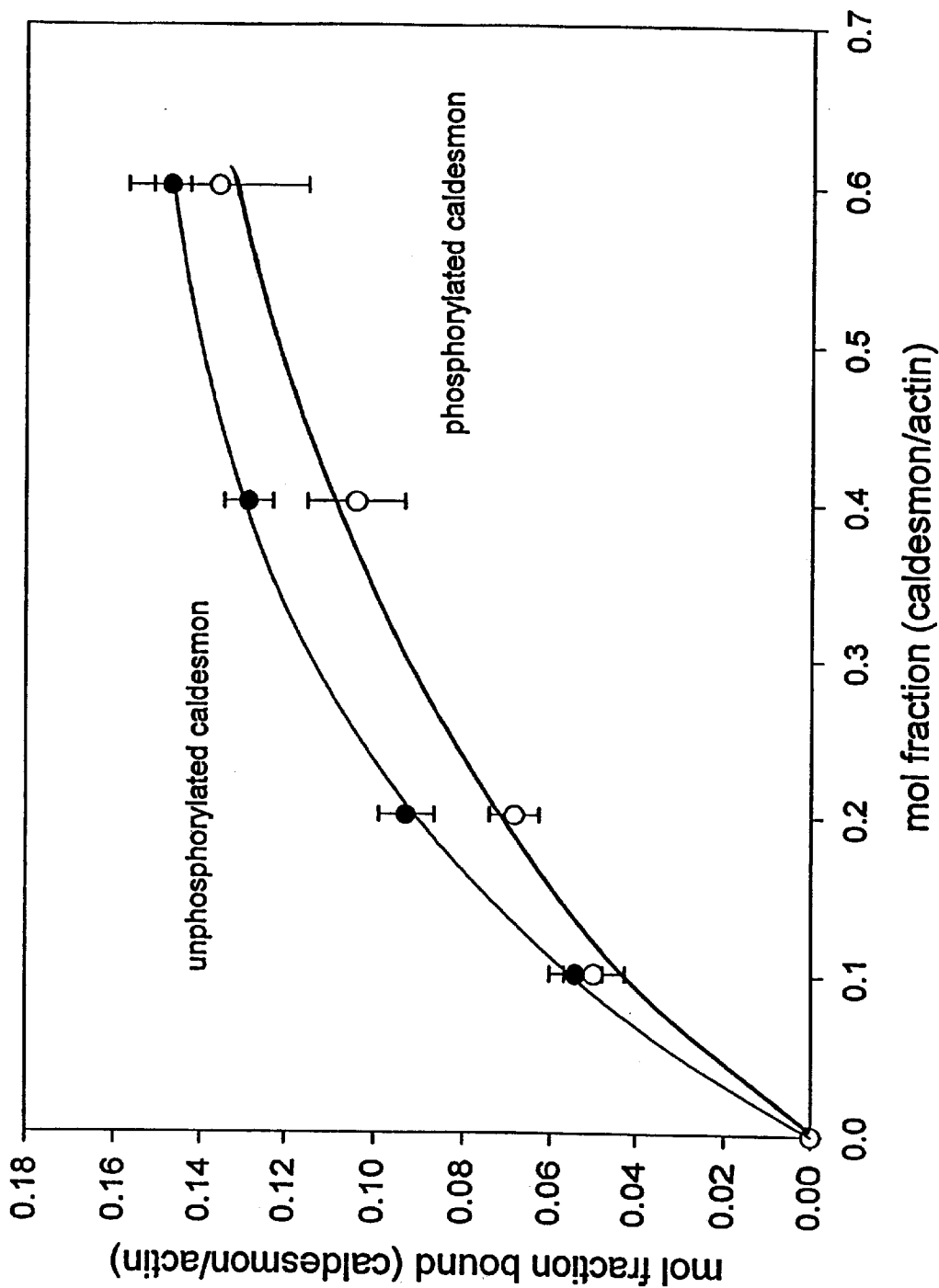

A=actin-TM-caldesmon filament
M=smooth muscle myosin
Mp= phosphorylated smooth muscle myosin at serine 19
MLCK=myosin light chain kinase
MLCP=myosin light chain phosphatase HPLC trace if TnI contained 41186 cpm

FIGURE 14
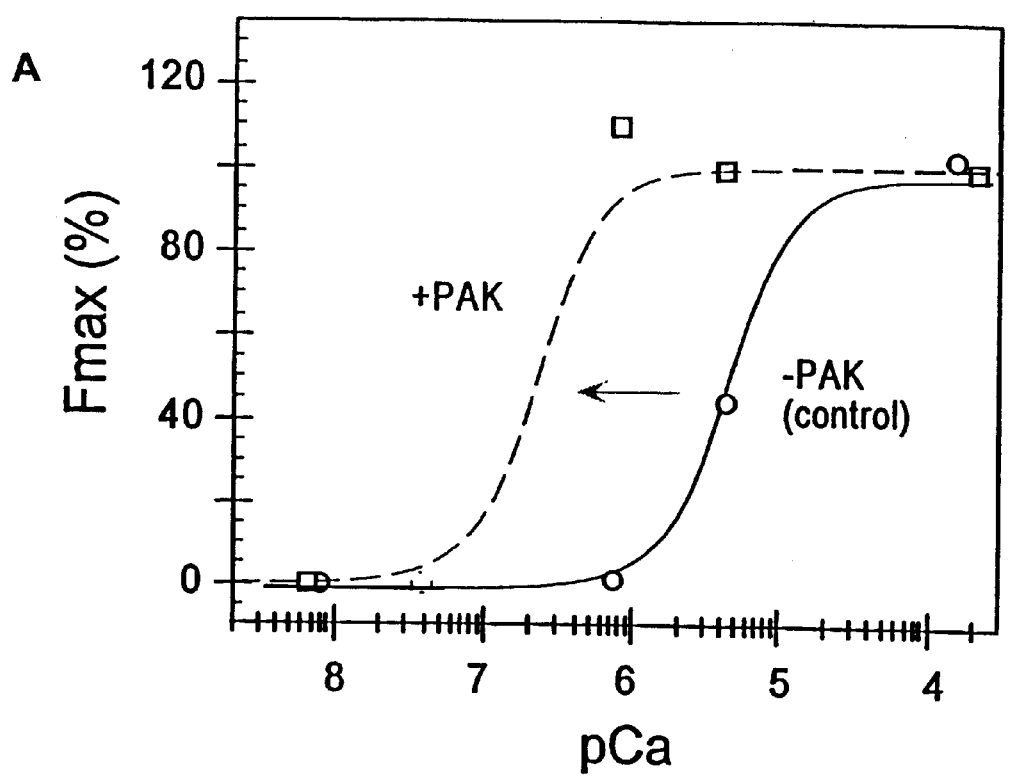
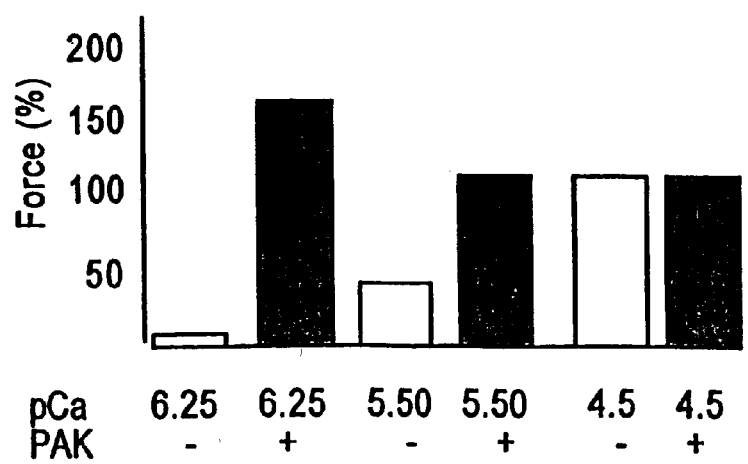

FIGURE 15
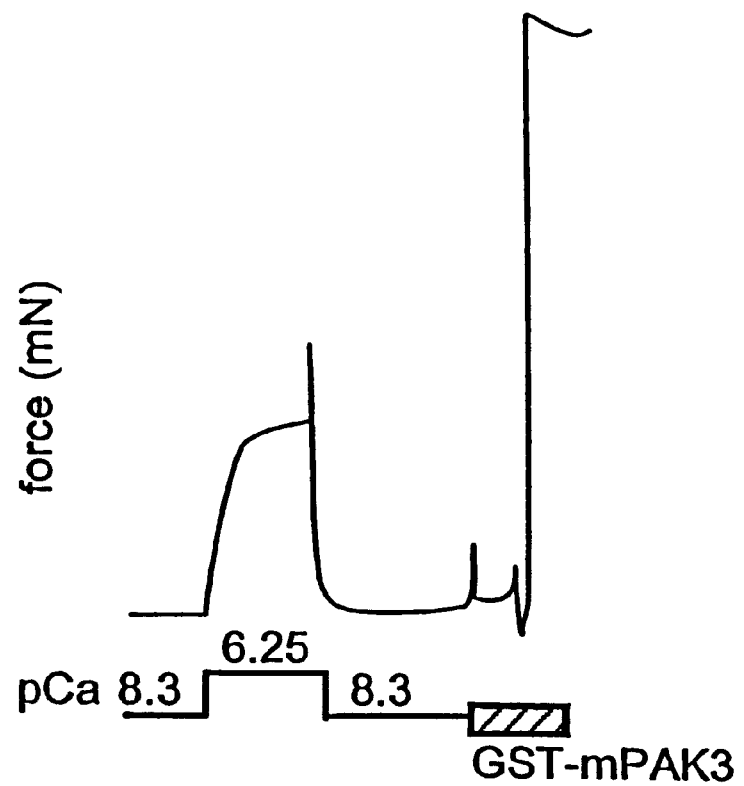
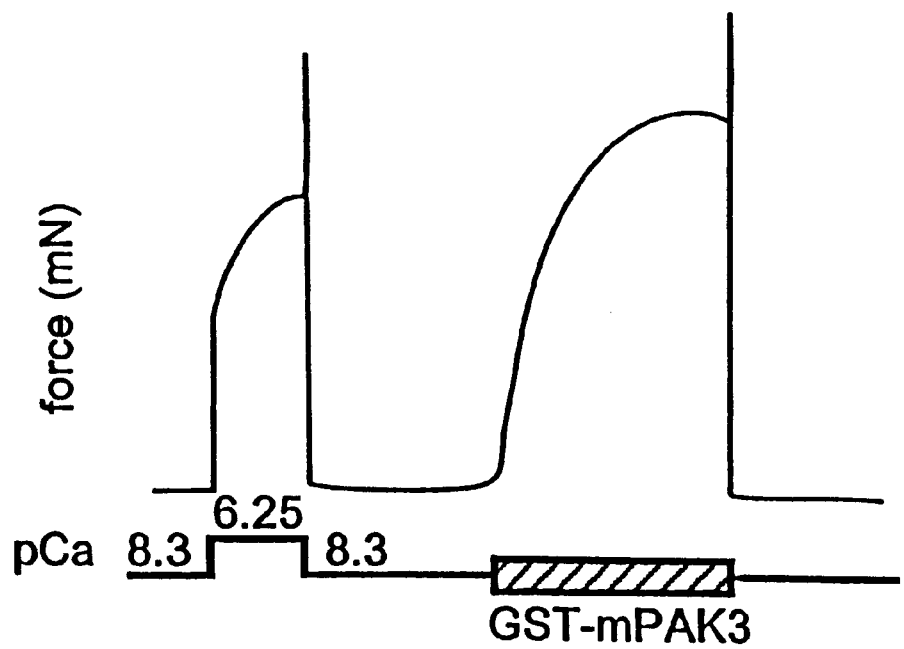

SEQUENCE LISTING

```
<160> NUMBER OF SEQ ID NOS:  26

<210> SEQ ID NO 1
<211> LENGTH: 28
<212> TYPE: PRT
<213> ORGANISM: Unknown
<220> FEATURE:
<221> NAME/KEY: PEPTIDE
<222> LOCATION: (1)..(28)
```

```
<223> OTHER INFORMATION: N-terminal truncation peptide based on PAK
<221> NAME/KEY: PEPTIDE
<222> LOCATION: (10)
<223> OTHER INFORMATION: Ala substituted for Cys in the native sequence
<221> NAME/KEY: PEPTIDE
<222> LOCATION: (22)
<223> OTHER INFORMATION: Targeted Thr phospho-amino acid

<400> SEQUENCE: 1

Ser Val Lys Leu Thr Asp Phe Gly Phe Ala Ala Gln Ile Thr Pro Glu
 1               5                  10                  15

Gln Ser Lys Arg Ser Thr Met Val Gly Thr Pro Tyr
            20                  25

<210> SEQ ID NO 2
<211> LENGTH: 21
<212> TYPE: PRT
<213> ORGANISM: Unknown
<220> FEATURE:
<221> NAME/KEY: PEPTIDE
<222> LOCATION: (1)..(21)
<223> OTHER INFORMATION: N-terminal truncation peptide based on PAK
<221> NAME/KEY: PEPTIDE
<222> LOCATION: (3)
<223> OTHER INFORMATION: Ala substituted for Cys in the native sequence
<221> NAME/KEY: PEPTIDE
<222> LOCATION: (15)
<223> OTHER INFORMATION: Targeted Thr phospho-amino acid

<400> SEQUENCE: 2

Gly Phe Ala Ala Gln Ile Thr Pro Glu Gln Ser Lys Arg Ser Thr Met
 1               5                  10                  15

Val Gly Thr Pro Tyr
            20

<210> SEQ ID NO 3
<211> LENGTH: 14
<212> TYPE: PRT
<213> ORGANISM: Unknown
<220> FEATURE:
<221> NAME/KEY: PEPTIDE
<222> LOCATION: (1)..(14)
<223> OTHER INFORMATION: N-terminal truncation peptide based on PAK
<221> NAME/KEY: PEPTIDE
<222> LOCATION: (8)
<223> OTHER INFORMATION: Targeted Thr phospho-amino acid

<400> SEQUENCE: 3

Pro Glu Gln Ser Lys Arg Ser Thr Met Val Gly Thr Pro Tyr
 1               5                  10

<210> SEQ ID NO 4
<211> LENGTH: 11
<212> TYPE: PRT
<213> ORGANISM: Unknown
<220> FEATURE:
<221> NAME/KEY: PEPTIDE
<222> LOCATION: (1)..(11)
<223> OTHER INFORMATION: N-terminal truncation peptide based on PAK
<221> NAME/KEY: PEPTIDE
<222> LOCATION: (5)
<223> OTHER INFORMATION: Targeted Thr phospho-amino acid

<400> SEQUENCE: 4

Ser Lys Arg Ser Thr Met Val Gly Thr Pro Tyr
 1               5                  10

<210> SEQ ID NO 5
<211> LENGTH: 4
```

```
-continued

<212> TYPE: PRT
<213> ORGANISM: Unknown
<220> FEATURE:
<221> NAME/KEY: PEPTIDE
<222> LOCATION: (1)..(4)
<223> OTHER INFORMATION: Sequence phosphorylated by PAK1
<221> NAME/KEY: PEPTIDE
<222> LOCATION: (1)
<223> OTHER INFORMATION: May be either Arg or Lys
<221> NAME/KEY: PEPTIDE
<222> LOCATION: (2)
<223> OTHER INFORMATION: May be either Arg or Lys
<221> NAME/KEY: PEPTIDE
<222> LOCATION: (3)
<223> OTHER INFORMATION: May be any amino acid.

<400> SEQUENCE: 5

Xaa Xaa Xaa Ser
 1

<210> SEQ ID NO 6
<211> LENGTH: 4
<212> TYPE: PRT
<213> ORGANISM: Unknown
<220> FEATURE:
<221> NAME/KEY: PEPTIDE
<222> LOCATION: (1)..(4)
<223> OTHER INFORMATION: Sequence phosphorylated by PAK1
<221> NAME/KEY: PEPTIDE
<222> LOCATION: (1)
<223> OTHER INFORMATION: May be either Arg or Lys
<221> NAME/KEY: PEPTIDE
<222> LOCATION: (2)
<223> OTHER INFORMATION: May be either Arg or Lys
<221> NAME/KEY: PEPTIDE
<222> LOCATION: (3)
<223> OTHER INFORMATION: May be any amino acid.
<221> NAME/KEY: PEPTIDE
<222> LOCATION: (4)
<223> OTHER INFORMATION: May be either Ser or Thr

<400> SEQUENCE: 6

Xaa Xaa Xaa Xaa
 1

<210> SEQ ID NO 7
<211> LENGTH: 14
<212> TYPE: PRT
<213> ORGANISM: Unknown
<220> FEATURE:
<221> NAME/KEY: PEPTIDE
<222> LOCATION: (1)..(14)
<223> OTHER INFORMATION: Residues 25 to 38 of cardiac TnI
<221> NAME/KEY: PEPTIDE
<222> LOCATION: (14)
<223> OTHER INFORMATION: Targeted Ser phospho-amino acid

<400> SEQUENCE: 7

Tyr Arg Ala Tyr Ala Thr Glu Pro His Ala Lys Lys Lys Ser
 1               5                  10

<210> SEQ ID NO 8
<211> LENGTH: 19
<212> TYPE: PRT
<213> ORGANISM: Unknown
<220> FEATURE:
<221> NAME/KEY: PEPTIDE
<222> LOCATION: (1)..(19)
<223> OTHER INFORMATION: Residues 147 to 164 of cardiac TnI
<221> NAME/KEY: PEPTIDE
<222> LOCATION: (19)
<223> OTHER INFORMATION: Targeted Ser phospho-amino acid
```

```
<400> SEQUENCE: 8

Arg Ile Ser Ala Asp Ala Met Met Gln Ala Leu Leu Gly Ala Arg Ala
 1               5                  10                  15

Lys Glu Ser

<210> SEQ ID NO 9
<211> LENGTH: 17
<212> TYPE: PRT
<213> ORGANISM: Unknown
<220> FEATURE:
<221> NAME/KEY: PEPTIDE
<222> LOCATION: (1)..(17)
<223> OTHER INFORMATION: Residues 7 to 22 of human cardiac TnI
<221> NAME/KEY: PEPTIDE
<222> LOCATION: (17)
<223> OTHER INFORMATION: Targeted Ser phospho-amino acid

<400> SEQUENCE: 9

Ala Ala Arg Glu Pro Arg Pro Ala Pro Ala Pro Ile Arg Arg Arg Ser
 1               5                  10                  15

Ser

<210> SEQ ID NO 10
<211> LENGTH: 11
<212> TYPE: PRT
<213> ORGANISM: Unknown
<220> FEATURE:
<221> NAME/KEY: PEPTIDE
<222> LOCATION: (1)..(11)
<223> OTHER INFORMATION: Residues 423 to 433 of chicken gizzard
      caldesmon
<221> NAME/KEY: PEPTIDE
<222> LOCATION: (11)
<223> OTHER INFORMATION: Targeted Ser phospho-amino acid

<400> SEQUENCE: 10

Lys Glu Ala Lys Val Glu Ala Lys Lys Glu Ser
 1               5                  10

<210> SEQ ID NO 11
<211> LENGTH: 11
<212> TYPE: PRT
<213> ORGANISM: Unknown
<220> FEATURE:
<221> NAME/KEY: PEPTIDE
<222> LOCATION: (1)..(11)
<223> OTHER INFORMATION: Residues 592 to 602 of chicken gizzard and
      human caldesmon
<221> NAME/KEY: PEPTIDE
<222> LOCATION: (10)
<223> OTHER INFORMATION: Targeted Ser phospho-amino acid
<221> NAME/KEY: PEPTIDE
<222> LOCATION: (11)
<223> OTHER INFORMATION: Targeted Ser phospho-amino acid

<400> SEQUENCE: 11

Pro Phe Lys Cys Phe Ser Pro Lys Gly Ser Ser
 1               5                  10

<210> SEQ ID NO 12
<211> LENGTH: 6
<212> TYPE: PRT
<213> ORGANISM: Unknown
<220> FEATURE:
<221> NAME/KEY: PEPTIDE
<222> LOCATION: (1)..(6)
<223> OTHER INFORMATION: Residues 718 to 723 of chicken gizzard and
      human caldesmon
```

```
<400> SEQUENCE: 12

Pro Ala Pro Lys Pro Ser
 1               5

<210> SEQ ID NO 13
<211> LENGTH: 9
<212> TYPE: PRT
<213> ORGANISM: Unknown
<220> FEATURE:
<221> NAME/KEY: PEPTIDE
<222> LOCATION: (1)..(9)
<223> OTHER INFORMATION: Residues 751 to 759 of chicken gizzard
      caldesmon
<221> NAME/KEY: PEPTIDE
<222> LOCATION: (9)
<223> OTHER INFORMATION: Targeted Ser phospho-amino acid

<400> SEQUENCE: 13

Lys Val Thr Ala Thr Gly Lys Lys Ser
 1               5

<210> SEQ ID NO 14
<211> LENGTH: 10
<212> TYPE: PRT
<213> ORGANISM: Unknown
<220> FEATURE:
<221> NAME/KEY: PEPTIDE
<222> LOCATION: (1)..(10)
<223> OTHER INFORMATION: Site 1 of PAK65 or PAK1

<400> SEQUENCE: 14

Ser Lys Arg Ser Met Val Gly Thr Pro Tyr
 1               5                  10

<210> SEQ ID NO 15
<211> LENGTH: 19
<212> TYPE: PRT
<213> ORGANISM: Unknown
<220> FEATURE:
<221> NAME/KEY: PEPTIDE
<222> LOCATION: (1)..(19)
<223> OTHER INFORMATION: Site 2 of PAK65 or PAK1
<221> NAME/KEY: PEPTIDE
<222> LOCATION: (12)
<223> OTHER INFORMATION: Targeted Ser phospho-amino acid

<400> SEQUENCE: 15

Ser Val Asp Pro Val Pro Ala Pro Val Gly Asp Ser His Val Asp Gly
 1               5                  10                  15

Ala Ala Lys

<210> SEQ ID NO 16
<211> LENGTH: 5
<212> TYPE: PRT
<213> ORGANISM: Unknown
<220> FEATURE:
<221> NAME/KEY: PEPTIDE
<222> LOCATION: (1)..(5)
<223> OTHER INFORMATION: At position -4 or -5 of PAK
<221> NAME/KEY: PEPTIDE
<222> LOCATION: (2)
<223> OTHER INFORMATION: May be any amino acid.
<221> NAME/KEY: PEPTIDE
<222> LOCATION: (4)
<223> OTHER INFORMATION: May be any amino acid.

<400> SEQUENCE: 16

Pro Xaa Pro Xaa Pro
 1               5
```

```
<210> SEQ ID NO 17
<211> LENGTH: 4
<212> TYPE: PRT
<213> ORGANISM: Unknown
<220> FEATURE:
<221> NAME/KEY: PEPTIDE
<222> LOCATION: (1)..(4)
<223> OTHER INFORMATION: Site C of Pak1

<400> SEQUENCE: 17

Lys Tyr Met Ser
 1

<210> SEQ ID NO 18
<211> LENGTH: 4
<212> TYPE: PRT
<213> ORGANISM: Unknown
<220> FEATURE:
<221> NAME/KEY: PEPTIDE
<222> LOCATION: (1)..(4)
<223> OTHER INFORMATION: Site C of PAK3

<400> SEQUENCE: 18

Lys Tyr Leu Ser
 1

<210> SEQ ID NO 19
<211> LENGTH: 8
<212> TYPE: PRT
<213> ORGANISM: Unknown
<220> FEATURE:
<221> NAME/KEY: PEPTIDE
<222> LOCATION: (1)..(8)
<223> OTHER INFORMATION: Site G (catalytic site) autophosphorylation of
      PAK1

<400> SEQUENCE: 19

Thr Thr Pro Pro Lys Arg Ser Thr
 1               5

<210> SEQ ID NO 20
<211> LENGTH: 7
<212> TYPE: PRT
<213> ORGANISM: Unknown
<220> FEATURE:
<221> NAME/KEY: PEPTIDE
<222> LOCATION: (1)..(7)
<223> OTHER INFORMATION: Site G (catalytic site) of PAK3

<400> SEQUENCE: 20

Ser Gly Ala Lys Arg Ser Thr
 1               5

<210> SEQ ID NO 21
<211> LENGTH: 18
<212> TYPE: PRT
<213> ORGANISM: Unknown
<220> FEATURE:
<221> NAME/KEY: PEPTIDE
<222> LOCATION: (1)..(18)
<223> OTHER INFORMATION: Consensus phosphorylation site of smooth muscle
      MLCK
<221> NAME/KEY: PEPTIDE
<222> LOCATION: (1)
<223> OTHER INFORMATION: May be either Lys or Arg
<221> NAME/KEY: PEPTIDE
<222> LOCATION: (2)
<223> OTHER INFORMATION: May be either Lys or Arg
<221> NAME/KEY: PEPTIDE
```

```
<222> LOCATION: (3)
<223> OTHER INFORMATION: May be any amino acid.
<221> NAME/KEY: PEPTIDE
<222> LOCATION: (4)
<223> OTHER INFORMATION: May be any amino acid.
<221> NAME/KEY: PEPTIDE
<222> LOCATION: (5)
<223> OTHER INFORMATION: May be absent or present; may be any amino
      acid.
<221> NAME/KEY: PEPTIDE
<222> LOCATION: (6)
<223> OTHER INFORMATION: May be either Lys or Arg
<221> NAME/KEY: PEPTIDE
<222> LOCATION: (7)
<223> OTHER INFORMATION: May be either Lys or Arg
<221> NAME/KEY: PEPTIDE
<222> LOCATION: (8)
<223> OTHER INFORMATION: May be either Lys or Arg
<221> NAME/KEY: PEPTIDE
<222> LOCATION: (9)
<223> OTHER INFORMATION: May be any amino acid.
<221> NAME/KEY: PEPTIDE
<222> LOCATION: (10)
<223> OTHER INFORMATION: May be any amino acid.
<221> NAME/KEY: PEPTIDE
<222> LOCATION: (11)
<223> OTHER INFORMATION: May be absent or present; may be any amino
      acid.
<221> NAME/KEY: PEPTIDE
<222> LOCATION: (13)
<223> OTHER INFORMATION: May be any amino acid.
<221> NAME/KEY: PEPTIDE
<222> LOCATION: (14)
<223> OTHER INFORMATION: May be any amino acid.

<400> SEQUENCE: 21

Xaa Xaa Xaa Xaa Xaa Xaa Xaa Xaa Xaa Xaa Xaa Arg Xaa Xaa Ser Asn
 1               5                  10                  15

Val Phe

<210> SEQ ID NO 22
<211> LENGTH: 9
<212> TYPE: PRT
<213> ORGANISM: Unknown
<220> FEATURE:
<221> NAME/KEY: PEPTIDE
<222> LOCATION: (1)..(9)
<223> OTHER INFORMATION: PAK site A autophosphorylation
<221> NAME/KEY: PEPTIDE
<222> LOCATION: (9)
<223> OTHER INFORMATION: Targeted Ser phospho-amino acid

<400> SEQUENCE: 22

Pro Ala Pro Pro Met Arg Asn Thr Ser
 1               5

<210> SEQ ID NO 23
<211> LENGTH: 8
<212> TYPE: PRT
<213> ORGANISM: Unknown
<220> FEATURE:
<221> NAME/KEY: PEPTIDE
<222> LOCATION: (1)..(8)
<223> OTHER INFORMATION: PAK Site E autophosphorylation
<221> NAME/KEY: PEPTIDE
<222> LOCATION: (8)
<223> OTHER INFORMATION: Targeted Ser phospho-amino acid

<400> SEQUENCE: 23

Pro Arg Pro Glu His Thr Lys Ser
 1               5
```

```
<210> SEQ ID NO 24
<211> LENGTH: 9
<212> TYPE: PRT
<213> ORGANISM: Unknown
<220> FEATURE:
<221> NAME/KEY: PEPTIDE
<222> LOCATION: (1)..(9)
<223> OTHER INFORMATION: Residues 25 to 38 of TnI
<221> NAME/KEY: PEPTIDE
<222> LOCATION: (9)
<223> OTHER INFORMATION: Targeted Ser phospho-amino acid

<400> SEQUENCE: 24

Thr Glu Pro His Ala Lys Lys Lys Ser
 1               5

<210> SEQ ID NO 25
<211> LENGTH: 13
<212> TYPE: PRT
<213> ORGANISM: Unknown
<220> FEATURE:
<221> NAME/KEY: PEPTIDE
<222> LOCATION: (1)..(13)
<223> OTHER INFORMATION: Residues 7 to 22 of human cTnI
<221> NAME/KEY: PEPTIDE
<222> LOCATION: (12)
<223> OTHER INFORMATION: Targeted Ser phospho-amino acid
<221> NAME/KEY: PEPTIDE
<222> LOCATION: (13)
<223> OTHER INFORMATION: Targeted Ser phospho-amino acid

<400> SEQUENCE: 25

Pro Arg Pro Ala Pro Ala Pro Ile Arg Arg Arg Ser Ser
 1               5                  10

<210> SEQ ID NO 26
<211> LENGTH: 10
<212> TYPE: PRT
<213> ORGANISM: Unknown
<220> FEATURE:
<221> NAME/KEY: PEPTIDE
<222> LOCATION: (1)..(10)
<223> OTHER INFORMATION: Consensus sequence determined for
      phosphorylation by PAK
<221> NAME/KEY: PEPTIDE
<222> LOCATION: (2)
<223> OTHER INFORMATION: May be any amino acid.
<221> NAME/KEY: PEPTIDE
<222> LOCATION: (5)
<223> OTHER INFORMATION: May be any amino acid.
<221> NAME/KEY: PEPTIDE
<222> LOCATION: (6)
<223> OTHER INFORMATION: May be absent or present; may be any amino
      acid.
<221> NAME/KEY: PEPTIDE
<222> LOCATION: (7)
<223> OTHER INFORMATION: May be either Arg or Lys
<221> NAME/KEY: PEPTIDE
<222> LOCATION: (8)
<223> OTHER INFORMATION: May be either Arg or Lys
<221> NAME/KEY: PEPTIDE
<222> LOCATION: (9)
<223> OTHER INFORMATION: May be any amino acid.
<221> NAME/KEY: PEPTIDE
<222> LOCATION: (10)
<223> OTHER INFORMATION: Targeted Ser phospho-amino acid

<400> SEQUENCE: 26

Pro Xaa Pro Pro Xaa Xaa Xaa Xaa Xaa Ser
 1               5                  10
```

METHODS OF MODULATING MUSCLE CONTRACTION

RELATED APPLICATIONS

This application claims the benefit of priority of U.S. Provisional Patent Applications No. 60/050,478, filed Jun. 23, 1997, and No. 60/089,505 filed Jun. 16, 1998. The contents of both these provisional applications are incorporated herein by reference.

FIELD OF THE INVENTION

This invention relates to methods for modulating muscle contraction, and particularly, to methods for modulating smooth muscle contraction in the absence of calcium, and for increasing the calcium sensitivity of both smooth muscle and cardiac muscle.

BACKGROUND OF THE INVENTION p21-activated kinase (PAK) proteins are serine/threonine protein kinases homologous to the yeast Ste20 kinase. Several distinct members of the PAK family have been identified in mammalian cells, including PAK1, PAK2, PAK3, and PAK65. It has been shown that PAK proteins can be activated by the small Rho-family GTP-binding proteins Cdc42 and Rac1, which are known to regulate assembly of the actin cytoskeletal structure (Zhang et al. 1995, *J. Biol. Chem.* 270:23934–36).

Smooth muscle, in contrast to striated muscle (cardiac and skeletal muscle), is capable of maintaining force at low levels of intracellular calcium. One member of the small Rho-family of GTP-binding proteins, RhoA, has been shown recently to induce smooth muscle contraction independently of calcium. RhoA activates a serinet reonine kinase named ROK (RhoA associated kinase or p160ROK) which can cause smooth muscle calcium-independent contraction. Cardiac muscle, on the other hand, requires increased levels of intracellular calcium for contraction.

Smooth muscle is found in blood vessels, the airways of the lungs, the gastro-intestial tract, the uterus and the urinary tract. The uncontrolled contraction of smooth muscle in such tissues is involved in states such as hypertension (a known risk factor for heart disease), asthma, irritable bowel syndrome, incontinence or menstrual cramps. Hypertension or high blood pressure, is the most common disease affecting the heart and blood vessels. Statistics indicate that hypertension afflicts one out of every five American adults. Asthma is a chronic disease characterized by airway hyperactivity, it occurs in 5–8% of the U.S. population, and is an extraordinarily common cause of pulmonary impairment. Irritable bowel syndrome is a common syndrome characterized by frequently alternating constipation and diarrhea, usually with abdominal pain. Often stress induced, it is also caused by such physical factors as spicy foods, lack of dietary fiber, and excessive caffeine consumption. Incontinence is the lack of voluntary control over micturition. In infants it is normal because neurons to the external sphincter muscle are not completely developed. In the adult it may occur as a result of unconsciousness, injury to the spinal nerves controlling the urinary bladder, irritation due to abnormal constituents in urine, disease of the urinary bladder and inability of the detrusor muscle to relax due to emotional stress. Menstrual cramping is a painful spasmodic contraction of the uterine muscles.

Abnormal contraction in cardiac muscle is the basis of many heart diseases. Heart failure (HF) is a common heart disease caused mainly by coronary artery disease and hypertension. Because specific treatment is not possible for most patients, current therapies are designed to ameliorate the symptoms and/or forestall myocardial damage. This includes increasing myocardial contractility by increasing cardiac myofilament sensitivity to calcium (Nielsen, J. E. et al. 1995, *J. Cardiovasc. Phormacol.* 26:S77–S84). Changes in calcium sensitivity also occur with acute disease states including myocardial stunning. Stunning is a reversible mild form of ischemic (no blood flow) damage, and may be induced by physiological insult such as heart surgery. Severe ischemic damage occurs with myocardial infarction and results in changes to cardiac muscle function.

To date, treatments of the above mentioned states in smooth and cardiac muscle have not been completely effective.

SUMMARY OF THE INVENTION

The present invention is based, at least in part, on the discoveries that PAK induces contraction of smooth muscle in the absence of calcium and changes calcium sensitivity of cardiac muscle. These discoveries led to the methods of the invention.

By one aspect, the present invention provides methods for treating states characterized by smooth muscle contraction. These states characterized by smooth muscle contraction include states characterized by inappropriate smooth muscle contraction. The treatment can involve the reduction of or inhibition of inappropriate muscle contraction. Examples of such states include hypertension, asthma, irritable bowel syndrome, incontinence and menstrual cramps.

This invention pertains to a method of modulating smooth muscle contraction. The method involves administering a PAK modulating agent, e.g., PAK inhibitor, to a subject such that modulation of smooth muscle contraction occurs. A PAK inhibitor may be, for example, an agent which binds to, or blocks, either or both of the kinase domain of PAK and the p21 (e.g., Cdc42 or Rac1) binding domain of PAK, or the autophosphorylation sites of PAK, The smooth muscle is present preferably in a blood vessel, the airways of the lungs, the gastro-intestinal tract, the uterus or the urinary tract.

Another aspect of the invention pertains to a method of treating a subject having a state characterized by smooth muscle contraction. The method involves administering to a subject a therapeutically effective amount of a PAK modulating agent, e.g., PAK inhibitor, such that treatment of the state characterized by smooth muscle contraction occurs. In one embodiment, the smooth muscle has a high basal tone. In another embodiment, the state characterized by the contraction of smooth muscle involves abnormal or inappropriate contraction of smooth muscle. In yet another embodiment, the state characterized by the contraction of smooth muscle involves abnormal or inappropriate relaxation of smooth muscle. Finally, the state characterized by smooth muscle contraction is preferably hypertension, asthma, irritable bowel syndrome, incontinence or menstrual cramps.

Yet another aspect of the invention relates to a method of treating a subject having a heart condition associated with, or that could lead to, cardiac contractile dysfunction, for example, heart failure (HF). The method involves administering to a subject a therapeutically effective amount of a PAK modulating agent, e.g., a PAK stimulator or inhibitor, such that treatment of the heart condition occurs.

In yet another aspect, the invention provides assays, e.g., screening tests, to identify PAK or PAK modulating agents.

For example, screening tests of the invention can be used to quantify the amount of PAK or PAK mRNA present, i.e., PAK expression, within smooth muscle or cardiac muscle. Insofar as PAK expression can be used as an indicator of a condition, such as hypertension or HF, screening tests according to the invention are therefore usefull in assessing, for example, the disease state of an individual.

Screening tests of the invention are also useful for detecting or identifying, for example, modulating agents which are inhibitors, or alternatively, stimulators, of PAK kinase expression or activity. In a preferred embodiment, the screening assay identifies agents that modulate the kinase activity of a PAK protein. For example, the invention provides a method involving providing an indicator composition comprising a PAK protein having PAK kinase activity. The method further includes contacting the indicator composition with a test agent, and determining the effect of the test agent on PAK kinase activity in the indicator composition to thereby identify a compound that modulates the kinase activity of a PAK protein. A statistically significant change, such as a decrease or increase, in the level of PAK kinase activity in the presence of the test agent (relative to what is detected in the absence of the test agent) is indicative of the test agent being a PAK modulating agent. The indicator composition can be, for example, a smooth muscle cell, a smooth muscle cell extract or a detergent-skinned smooth muscle fiber bundle system. Screening tests in accordance with the invention can involve identifying the phosphorylation state of downstream target proteins such as, for example, caldesmon (CAD) or a fragment thereof. Thus, in one embodiment, PAK kinase activity is assessed by measuring phosphorylation of CAD. In another embodiment, PAK kinase activity is assessed by measuring phosphorylation of the myosin light chain ($LC_{20}$) or a fragment thereof. In still a further embodiment, PAK kinase activity is assessed by measuring phosphorylation of the calponin protein or a fragment thereof and/or another target protein, such as, for example, troponin I (or a fragment thereof) in cardiac muscle.

Other features and advantages of the invention will be apparent from the following detailed description, and from the claims.

BRIEF DESCRIPTION OF THE DRAWINGS

Embodiments of the invention will now be described, by way of example, with reference to the accompanying drawings, wherein:

FIG. 2 shows that constitutively active GST-mPAK3 induces $Ca^{2+}$-independent contraction of guinea pig taenia coli Triton X-100 skinned muscle fibers without involving myosin light chain kdnase (MLCK) or myosin light chain phosphatase (MLCP).

FIG. 3B shows time courses of in vitro phosphorylation of isolated smooth muscle $LC_{20}$ in the presence (●) or absence (○) of GST-mPAK3 followed by the addition of MLCK after 30 min (* Indicates time at which samples analyzed in FIG. 3C were obtained).

FIG. 3D is a plot of smooth muscle $LC_{20}$ phosphorylation (%) and the corresponding relative force (% of force relative to contracting conditions) obtained in the Triton X-100 skinned guinea pig taenia coli muscle fibers at pCa 4.3 (5, n=5) and pCa 8.3 in the absence (4, n=6) and presence of GST-mPAK3 (1–3, n=5) after a 90 minute incubation at 25° C. Experiments were done using five guinea pig Triton X-100 skinned taenia coli preparations and three different GST-mPAK3 preparations. Upper inset shows a typical western blot (using anti-$LC_{20}$ mAb) of a one-dimensional isoelectric focusing gel (2 to 3 fibers per lane, 18). The ratio of phosphorylated (mono- and di-phosphorylated protein) to unphosphorylated $LC_{20}$ was determined by densitometry. Standard curves were done to ensure the exposures of the western blots were within a linear range. Note: GST-mPAK3 causes an increase in force with no increase in $LC_{20}$ phosphorylation.

These autoradiographs were generated from the same blots used for western blotting with the anti-caldesmon or anti-desmin antibodies.

Figure 4A:
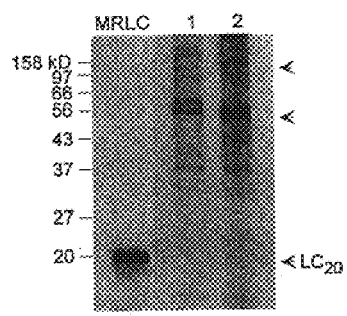
FIGS. 4A and 4B are autoradiographs of a 12% SDS-polyacrylamide gel analysis showing that phosphorylation of $LC_{20}$ by GST-ROK in the absence of calcium is similar to phosphorylation of $LC_{20}$ by MLCK at pCa 4.3.
Figure 4B:
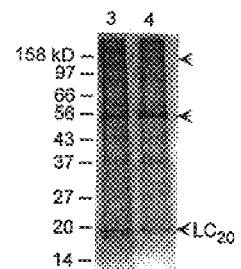
Figure 4C:
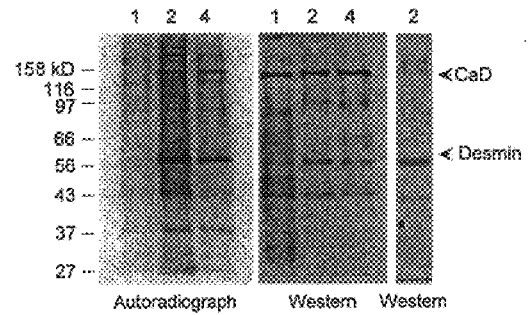
FIGS. 4C and 4D are autoradiographs of a 10% SDS-polyacrylamide gel analysis showing that caldesmon is the only protein phosphorylated by GST-mPAK3 that is not phosphorylated by GST-ROK in the skinned muscle fibers.
Figure 4D:
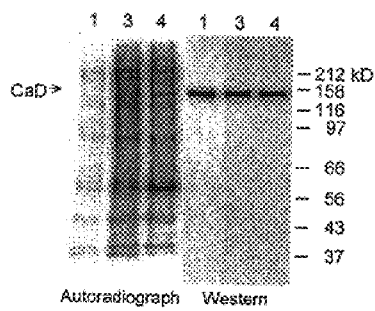
Figure 4E:
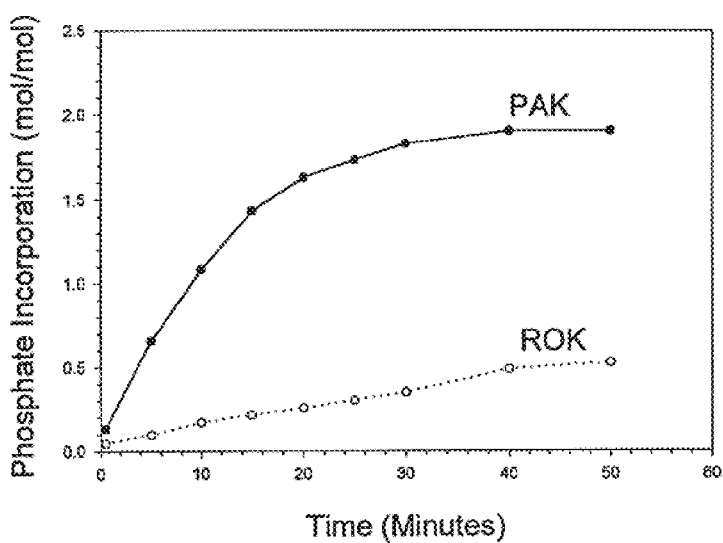
FIG. 4 shows that PAK (4A and 4C) and ROK (4B and 4D) phosphorylate different proteins in skinned smooth muscle fibers. In vitro PAK-phosphorylated $LC_{20}$ is included in 4A as a standard marker protein.

FIG. 4E shows the time course of in vitro phosphorylation of isolated chicken gizzard h-caldesmon (hCAD) by GST-mPAK3 (●) or GST-ROK (○).

Figure 4F:
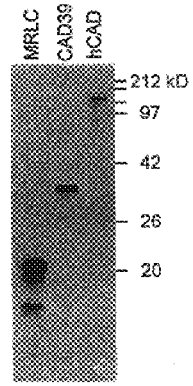

FIG. 4F shows an autoradiograph of a 12% SDS-polyacrylamide gel of $LC_{20}$, C-terminal fragment of caldesmon (CAD39), and intact chicken gizzard h-caldesmon phosphorylated in vitro by GST-mPAK3.

FIG. 5 shows a relationship between phosphorylation of caldesmon by PAK and the binding of caldesmon and actin. The data translate into an approximately two-fold reduction in the affinity of caldesmon for actin-tropomyosin.

Figure 6:
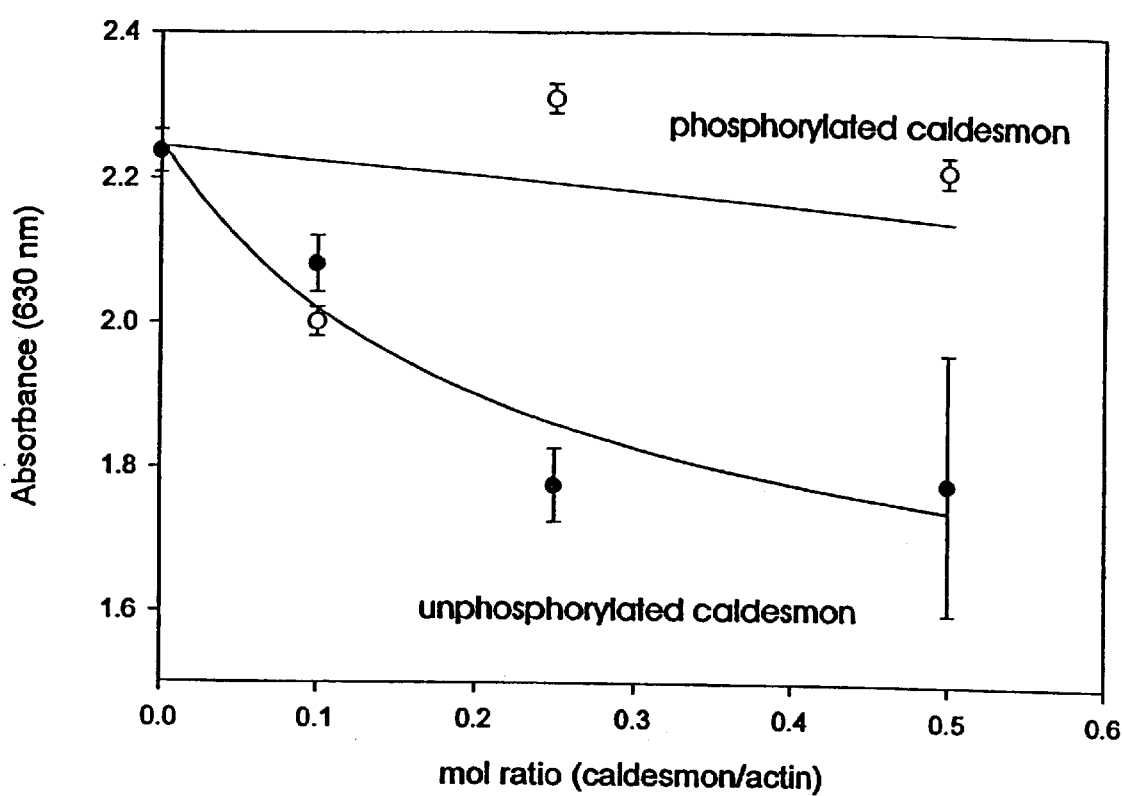

FIG. 6 is a graph showing that PAK-phosphorylated caldesmon is a poor inhibitor of myosin ATPase activity. Thus, phosphorylation of caldesmon disinhibits caldesmon which allows actin-tropomyosin to interact with myosin, increasing ATPase activity and resulting in contraction.

Figure 7:
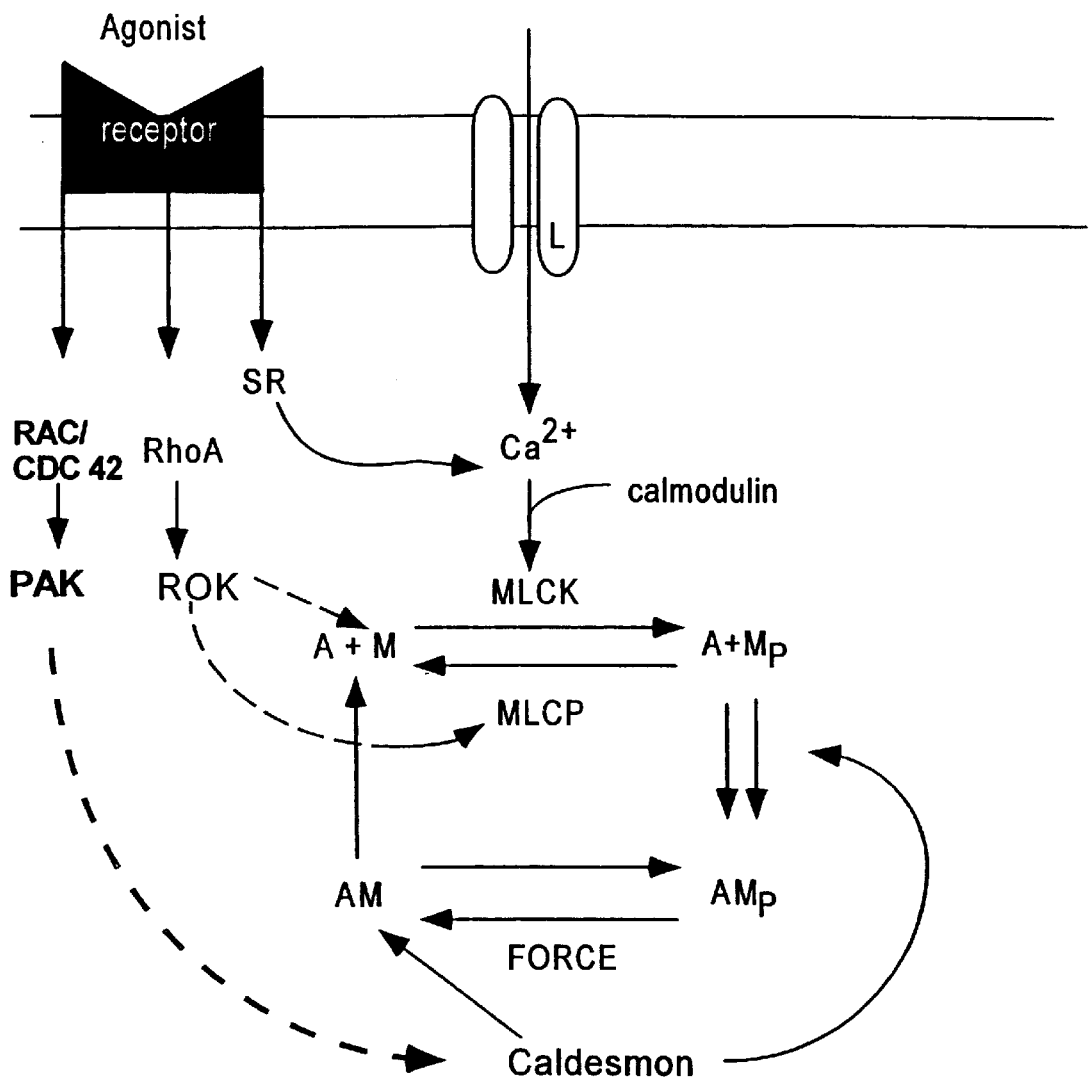

FIG. 7 is a schematic representation of a possible PAK pathway responsible for smooth muscle contraction.

Figure 8:
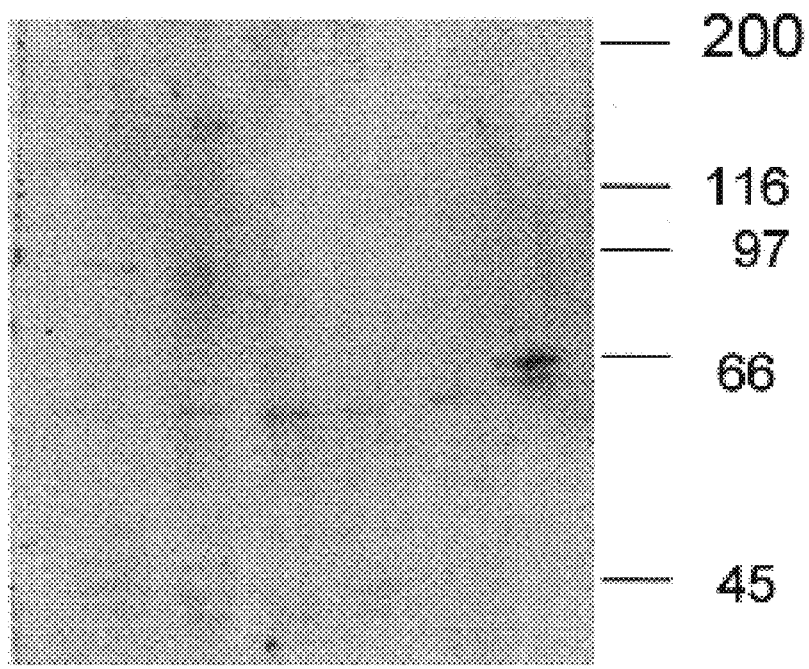

FIG. 8 shows the results of a gel overlay assay in which $GTP\gamma^{35}S$-Cdc42 bound to a~62kDa protein in porcine (P), dog (D), and rat (R) cardiac muscle, confirming the presence of PAK or a PAK homologue in cardiac muscle (C3, control-brain PAK; Sm, guinea pig smooth muscle; Rs, rat skinned muscle).

Figure 9:
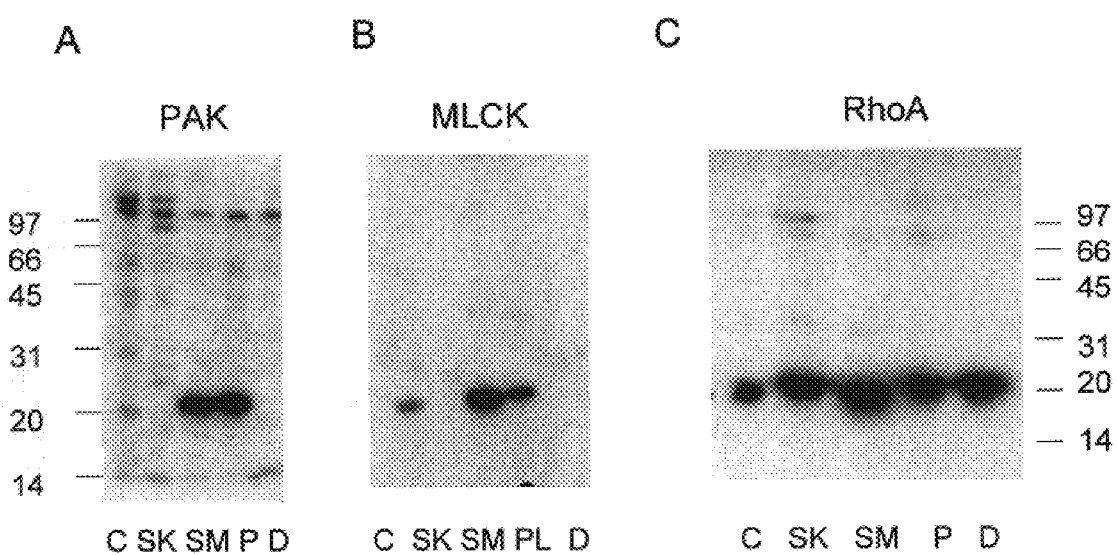

FIGS. 9A, B, and C show autoradiographs of in vitro phosphorylation of myosin isolated from various sources (C, cardiac; Sk, skeletal muscle; Sm, smooth muscle; P or Pl, platelet; D, Dictyostelium). $LC_{20}$ (about 20 kDa) is phosphorylated to various extents by PAK (FIG. 9A), MLC (FIG. 9B), and ROK (FIG. 9C). Cardiac muscle $LC_{20}$ is phosphorylated by MLCK and ROK, but poorly by PAK.

Figure 10:
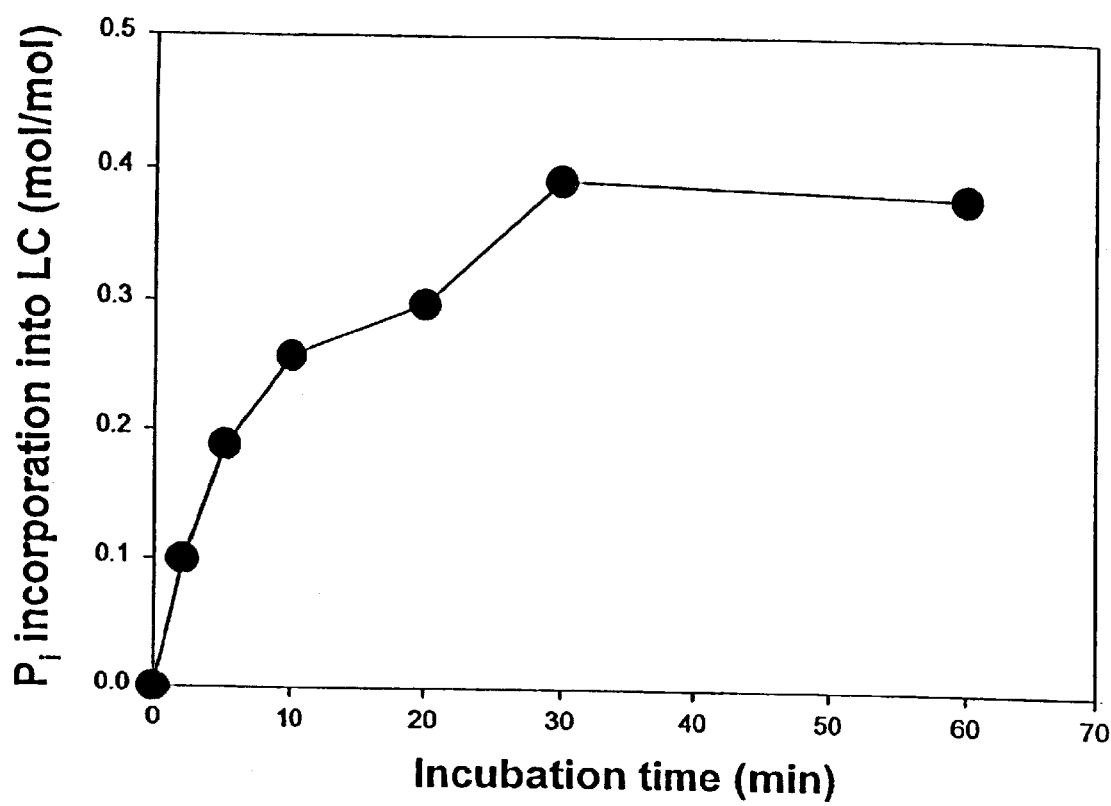

FIG. 10 shows the time course of phosphorylation of cardiac $LC_{20}$ by GST-ROK, up to 0.5 mol phosphate per mol protein.

Figure 11:
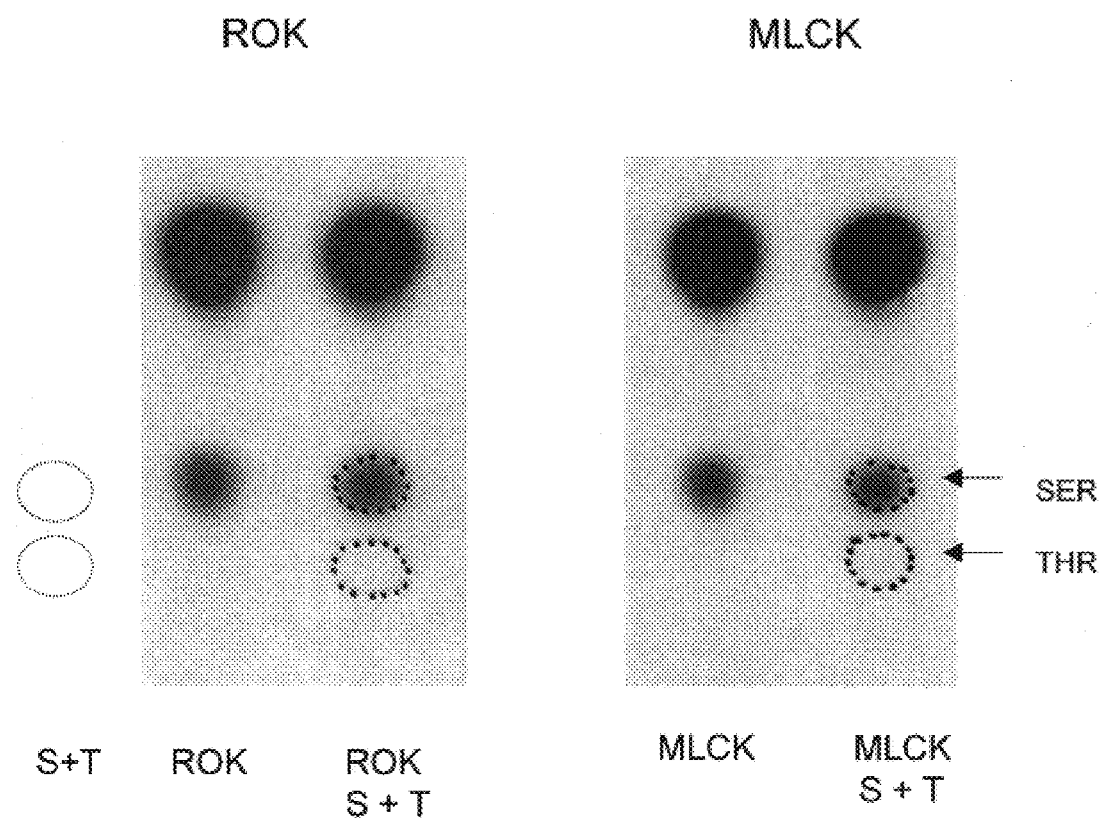

FIG. 11 shows the results of a phospho-amino acid analysis for cardiac $LC_{20}$, in which it can be seen that it is the same serine that is phosphorylated by both MLCK and GST-ROK.

FIGS. 12A, B, and C show tryptic peptide maps produced from cardiac $LC_{20}$ phosphorylated by MLCK, ROK, and MLCK and ROK, respectively.

Figure 13:
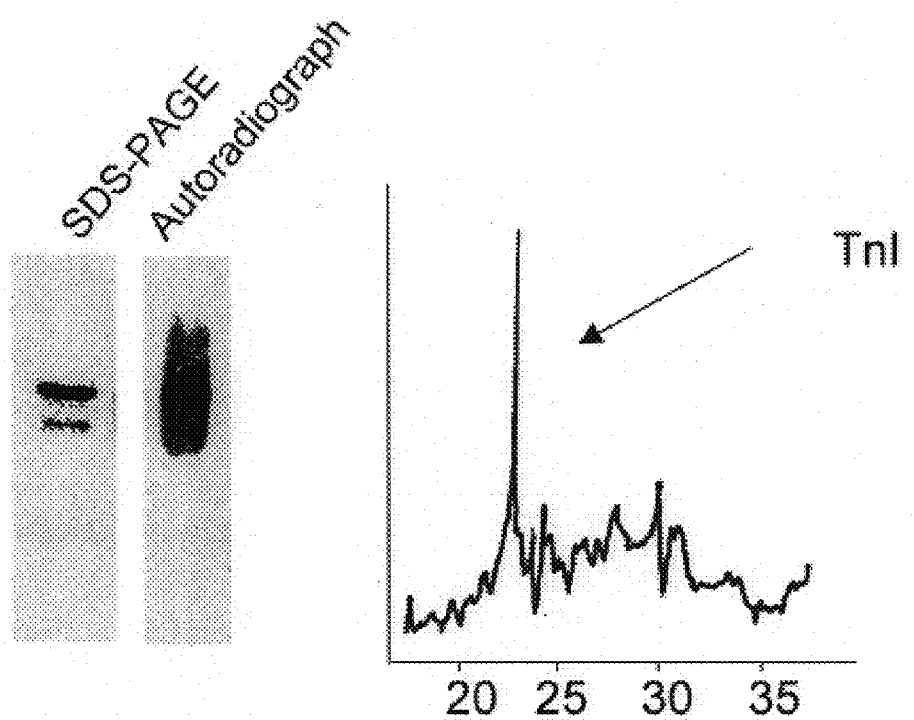

FIG. 13 is an autoradiograph showing in vitro phosphorylation of cardiac tropordn I(TnI). Cardiac Tn complex (TnI, TnT, and TnC) was phosphorylated by GST-mPAK in the presence of $^{32}$P-ATP, and TnI isolated by reversed phase HPLC.

FIGS. 14A and 14B show that the force produced by Triton X-100 skinned cardiac muscle fiber bundles increases in the prsence of GST-mPAK3, at calcium concentrations that produce submaximal contraction.

FIG. 15 is an exemplary trace showing increased calcium sensitivity of cardiac muscle contraction in the presence of GST-mPAK.

DETAILED DESCRIPTION

According to one aspect of the present invention there is provided a method of modulating smooth muscle contraction, e.g., calcium independent. The method involves administering a PAK modulating agent to a subject such that modulation of smooth muscle contraction occurs.

The language "smooth muscle" is intended to include smooth muscle sensitive to the PAK modulating agents of the present invention. Smooth muscle is sensitive to a PAK modulating agent if the agent modulates the contraction of the smooth muscle. Examples of smooth muscle include smooth muscle of a blood vessel, the airways of the lungs, the gastro-intestinal tract, the uterus, and the urinary tract.

As used herein, the language "modulating smooth muscle contraction" is intended to include the capacity to inhibit or stimulate smooth muscle contraction to various levels, e.g., which allows for the treatment of targeted states. The language is also intended to include the inducement of relaxation of smooth muscle, e.g., total relaxation, and the contraction of smooth muscle which is in relaxed state and it is desired to have the muscle in a more contracted state, e.g., the sphincter in esophageal reflux.

According to another aspect of the present invention, there is provided a method of modulating cardiac muscle contraction by changing the calcium sensitivity of cardiac muscle. The method involves administering a PAK modulating agent to a subject such that a change in calcium sensitivity of cardiac muscle, and hence modulation of contraction of cardiac muscle, occurs. A PAK modulating agent is an agent which enhances, or reduces, the expression of PAK or a PAK homologue present in cardiac muscle, or an agent which stimulates or inhibits the activity of PAK or a PAK homologue in cardiac muscle.

As used herein, the expression "change in calcium sensitivity of cardiac muscle" means a change in the amount (intracellular concentration) of calcium necessary to elicit cardiac muscle contraction of a given level of force. The change may be an increase in calcium sensitivity, such that a lower calcium concentration, relative to a normal physiological cardiac calcium concentration, will elicit cardiac muscle contraction with a given level of force, Alternatively, the change may be a decrease in calcium sensitivity, such that a higher calcium concentration, relative to a normal physiological cardiac calcium concentration, will elicit cardiac muscle contraction with a given level of force. A normal physiological cardiac calcium concentration refers to the concentration of calcium normally present in cardiac muscle of an individual not subjected to the methods of the present invention.

As used herein, the terms "subject" and "individual" are intended to include animals, preferably mammals, most preferably humans. In a preferred embodiment, the subject is a primate. In an even more preferred embodiment, the primate is a human.

As used herein, the language "PAK modulating agent" includes an agent which interacts with a p21-activated kinase and affects its activity. The modulating agent can be an inhibitor or a potentiator. As used herein, the language "PAK inhibitor" is intended to include agents which inhibit a PAK kinase. Examples of agents that inhibit serine/threonine kinase that may accordingly inhibit PAK, include Staurosporin, PD098059, Genistein, tyrphostin B42, HA1077, K252a, H-7. Examples of agents that may inhibit PAK expression are PAK specific antisense nucleic acids, ribozymes, intracellular antibodies, proteins, peptides, and protein fragments. These are described in detail below.

Examples of PAK inhibitors of serine/threonine kinases that are potentially useful within the method of the invention include Staurosporin, PD098059, Genistein, tyrphostin B42, HA1077, K252a, H-7: (1(5-isoquinoline-sulfonyl)-2-methylpiperazine) and the like, including analogues, derivatives and mimetics thereof that retain the ability to inhibit the PAK kinase.

One form of PAK inhibitors is peptide inhibitors. Peptide inhibitors of protein kinases, such as myosin light chain kinase (MLCK) and CAM kinase, are well known in the art (Kemp, B. E. et al. 1991. In: *Methods in Enzymology*, Vol. 201, pp. 287–304; Saitoh, M. et al. 1987. *J. Biol. Chem.* 262:7796–7801; Nakanishi, S. et al. 1992. *J. Biol. Chem.* 267:2157–2163; Strauss, J. D. et al. 1992. *Am. J. Physiol.* 262:C1437–C1445). Many protein kinases regulate themselves trough intermolecular autoinhibition (e.g., Johnson, L. N. et al. 1996. *Cell* 85:149–158; Kemp, B. E. et al. 1994. *Trends in Biochem. Sci.* 19:440–444), in which inhibition is achieved via the interaction of amino acid sequences within the kinase which act as pseudosubstrates which block the catalytic domain of the kinase. The Kinase remains inhibited until a specific Ser, Thr, or Tyr residue(s) located in the pseudosubstrate is phosphorylated (autophosphorylation), or until interaction with an effector eliminates binding of the pseudosubstrate. In the case of PAK, autophosphorylation occurs following binding of Cdc42/Rac1 and the subsequent conformation changes due to this interaction. The autophosphorylation sites of PAK3 and PAK2 have been identified, and PAK3 contains six Ser/Thr sites that are autophosphorylated (Manser, E. et al. 1997. *Mol. Cell Biol.* 17:1129–1143; Benner, G. E. et al. 1995. *J. Biol. Chem.* 270:270:21121–21128). For example, Thr422 of PAK3 is essential for catalytic activity. The regions around these Ser/Thr sites are regulatory domains that bind at the substrate binding site, and autophosphorylation fully opens the catalytic site. The amino acid sequence surrounding Thr422 is conserved in all PAK isoforms, further evidence that this sequence is recognizable by PAK. Thus, synthetic peptide inhibitors of PAK can be peptides having at least one amino acid sequence corresponding to at least one of these regulatory domains, but with the phosphorylatable Ser rreplaced by another amino acid that is not phosphorylatable, such that the peptide acts as a "dead-end" pseudosubstrate and inhibits PAK. Preferably, amino acids used to replace the Ser/Thr are Asp/Glu or Ala Since PAK can not phosphorylate such peptides, they act as competitive inhibitors. Suitable synthesized peptides include about 10 to 40 amino acids, typically about 12 to 20 amino acids.

Peptide inhibitors of PAK can thus be synthesized based on PAK substrates, either exogenous ($LC_{20}$ and CAD) or troponin I, or intramolecular (i.e., autophosphorylation/autoinhibitory sites). As well, peptide inhibitors of PAK can be peptides that compete for Cdc42 or Rac1 binding sites of PAK. In any case, peptide inhibitors of PAK are non-phosphorylatable analogues or pseudosubstrates of PAK substrates.

Kinases regulated by autophosphorylation may contain several amino acid residues in addition to the autoinhibitory sequence that are important for substrate recognition (Johnson, L. N. et al. 1996. *Cell* 85:149–158; Kemp, B. E. et al. 1994. *Trends in Biochem. Sci.* 19:440–444). For instance, an important basic amino acid is situated between the autoinhibitory region and the catalytic domain. In the PAK sequence there are two possible Lys residues that meet this criterion. Thus, the synthetic peptides can also include either or both of the two possible candidate residues. In these peptides, Cys is preferably substituted with Ala to minimize oxidation problems and disulfide bridge formation. Also, the N- and C-termini of all peptides are preferably acetylated and amidated, respectively, to eliminate effects form extra charges. This is especially preferred for small peptides, particularly as the minimum functional sequence is approached.

The minimum phosphorylatable amino acid sequence of a synthesized peptide that is actively phosphorylated by PAK can be determined using a series of N- and C-terminal truncation analogues. For example, an N-terminal truncation peptide series based on the PAK sequence (Tuazon, P. T. et al. 1997. *Biochemistry* 36:16059–16064; Manser, E. et al. 1997. *Mol. Cell Biol.* 17:1129–1143; Bagrodia, S. et al. 1995. *J. Biol. Chem.* 270:22731–22737) can be established as follows:

| peptide 1. | SVKLTDFGF<u>A</u>AQITPEQS*K*RST*MVGTPY | (SEQ ID NO: 1) |
|---|---|---|
| peptide 2. | GF<u>A</u>AQITPEQS*K*RST*MVGTPY | (SEQ ID NO: 2) |
| peptide 3. | PEQS*K*RST*MVGTPY | (SEQ ID NO: 3) |
| peptide 4. | S*K*RST*MVGTPY | (SEQ ID NO: 4) |

<u>A</u> is an Ala substituted for Cys in the native sequence. *K* is a Lys(i.e., a basic residue) as discussed above. T* is the targeted Thr phospho-amino acid.

Synthetic peptide inhibitors modulators

It has been shown that PAK1 phosphorylates synthetic peptides with sequence (R/K)-(R/K)-X-S (SEQ ID NO:5) (Tuazon et al., 1997 *Biochemistry* 36:16059). All of the possible phosphorylation sites we have identified include this sequence, either conserved or semi-conserved. However, many other kinases including MLCK and PKA have the same or similar amino acid consensus sequence. To increase specificity of peptide inhibitors for PAK rather than other kinases including PKA and MLCK, an extension of the amino acid sequence past (R/K)-(R/K)-X-S/T (SEQ ID NO:6) is preferred.

In the first autoinhibitory region, one or more positively charged amino acid residues (Arg, R or Lys, K) upstream (towards the N-terminus) of the phosphorylated Ser or Thr are believed to play a role. Therefore, these are included in the initial screening of the peptides for TnI and caldesmon.

TnI:

As reported herein, skeletal TnI is not phosphorylated, and this is supported by lack of the (R/K)-(R/K)-X-S/T (SEQ ID NO:6) motif in its amino acid sequence. There are three regions of cardiac TnI which contain this motif. They are conserved between rat and human cardiac TnI. These regions terminate with amino acid residues Ser 22, 23, 38, and 164 of human cardiac TnI. Ser 22 and 23 are phosphorylated by protein kinase A (PKA) during β-adrenergic activation.

For cardiac TnI, there is an additional R or K situated upstream in relatively close proximity to two of these four Ser in human. The two regions are:

YRAYATEPHAKKKS* (SEQ ID NO:7) (residues 25–38); and

RISADAMMQALLGARAKES* (SEQ ID NO:8) (residues 147–164).

However, for Ser 22, 23 (Ser 21, 22 in rat) there is no upstream R or K present, indicating either that neither of these Ser are phosphorylated, or (more likely) that the additional positively charged residue is not critical.

However, Ser 22 and 23 of cardiac TnI are believed to represent a different conformationally preferred binding site for PAK, since there are three proline (Pro, P) residues situated at positions 11, 13, 15 and 17. It is likely that these induce a unique structure in TnI that is preferred by PAK (AAREPRPAPAPIRRRSS* (SEQ ID NO:9) residues 7–22 of human cardiac TnI). With myosin light chain $LC_{20}$, there are also Pro situated at −5 upstream of the target Ser, and upstream Pro occur at several of the autophosphorylation sites for PAK1 and 3.

Caldesmon:

Caldesmon has several possible PAK phosphorylation sites near the C-terminus of chicken gizzard h-CAD. Several of these sites are not present in human fibroblast caldesmon, but may be present in the smooth muscle isoform of human h-CAD. Based on the chicken gizzard h-CAD sequence, there are KEAKVEAKKES* (SEQ ID NO:10) (good match, residues 423–433), PFKCFSPKGS*S* (SEQ ID NO:11) (weakly conserved, residues 592–602), PAPKPS (SEQ ID NO:12) (residues 718–723) and KVTATGKKS* (SEQ ID NO:13) (residues 751–759). Two of these sites are phosphorylated by PAK. Two tryptic fragments of PAK phosphorylated chicken gizzard h-CAD have been isolated and amino acid sequencing of such will verify the actual phosphorylation sites. Note that these phosphorylation sites contain either a positively charged amino acid (K in these cases) or several prolines starting at −3 or −4 positions.

Autoinhibitory region of PAK 1/PAK 65

Importantly, the autoinhibitory region of PAK65 or PAK1 has been determined to be near or at SKRSMVGTPY (SEQ ID NO:14) (site 1) and SVDPVPAPVGDS*HVDGAAK (SEQ ID NO:15) (site 2). (Note that several amino acids were missing from site 1 in Benner et al., 1995. *J. Biol. Chem.* 270:21121–21128, but this error was corrected in a subsequent report of the cDNA sequence, Manser et al., 1997.) Site 1 is rapidly phosphorylated and site 2 is required for activation of PAK1. Site 1 is highly conserved in-all PAK isoforms but only the extreme N-terminal part of site 2 is. There are no basic amino acids within site 2 (which is part of the "preferred" consensus sequence later described by Tuazon et al., 1997). There is a series of PXPXP (SEQ ID NO:16) at position −4 or −5, and it is believed that those proline residues provide unique identification for PAK.

Further work on PAKa or PAK1 (Manser et al., 1997. Mol. Cell. Biology 17;1129) showed that there are up to 7 autophosphorylation sites. Two of these are the same as shown by Benner et al. Several of these sites are conserved between the 3 isoforms of PAK (including PAKβ which is PAK3). For PAK3, sites A, E and F are conserved; site C which is KYMS (SEQ ID NO:17) in PAK1 is changed to KYLS (SEQ ID NO:18) in PAK3; and site G (catalytic site) which is TTPPKRST (SEQ ID NO:19) in PAK1 is changed to SGAKRST (SEQ ID NO:20) in PAK3; while sites B and D are missing the key residues.

It is expected that PAK1 is a good model for PAK3 with respect to specificity or activity at the catalytic site, and differences between substrates that the two kinases can phosphorylate may be minimal. That is, the difference between specificity of PAK1 and PAK3 likely lies in another domain, such as SH domains, and in the actual cellular localization of the various isoforms of PAK. This means that the amino acid residues near the sites of phosphorylation of substrates for PAK1 and PAK3 are expected to be similar, if not the same. So, even if PAK3 does not contain all of the autophosphorylation sites that are present in PAK1, the consensus amino acid sequences for PAK1 or PAK3 are expected to be the same. Therefore, the amino acid sequences of PAK1 phosphorylation sites were employed in designing amino acid sequences for peptide substrates for PAK3.

Peptide with conformationally preferred PAK sites

For determining any important aspects of phosphorylation sites for PAK where upstream Pro residues likely provide an unique conformation, we compared the amino acid sequences. For smooth muscle MLCK, the consensus phosphotylation site is $(K/R)_2$-$X_{2-3}$-$(K/R)_3$-$X_{2-3}$-R-$X_2$-S-N-V-F (SEQ ID NO:21) (Kennelly et al. 1991. *J. Biol. Chem.* 266:15555) and does not have any proline residues, even though there are numerous positively charged amino acid residues near R and/or K. It is believed that there is a unique amino acid sequence/conformation for PAK that is not seen with other kinases of interest.

PAPPMRNTS* (SEQ ID NO:22) (site A autophosphorylation)

PRPEHTKS* (SEQ ID NO:23) (site E autophosphorylation)

TTPPKRST* (SEQ ID NO:19) (site G autophosphorylation)catalytic site

TEPHAKKKS* (SEQ ID NO:24) (residues 25–38 TnI)

PRPAPAPERRRS*S* (SEQ ID NO:25) residues 7–22 of human cTnI

PFKCFSPKGSS* (SEQ ID NO:11) (weakly conserved, residues 592–602 h-CAD)

PAPKPS* (SEQ ID NO:22) (residues 718–723 h-CAD)

Determination of the TnI and caldesmon phosphorylation sites permits an amino acid consensus sequence for this series of peptides to be determined. These are expected to be similar to $PXPPX_{1-2}(R/K)(R/K)XS*$ (SEQ ID NO:26). By changing the number of residues (range from 1–3) and amino acid composition of the X position, the optimal peptide substrate for PAK can be determined. Thus, the phosphorylatable Ser can be substituted with Asp, Ala and Gly to produce peptides expected to be inhibitors.

Opimization of Peptide sequence

The amino acid residues initially screened above are first truncated from the N-terminus to determine the minimum sequence required for substrate activity by PAK. Then, any residues other than K, R or P which may be important are substituted with other amino acid residues. Conservative changes in amino acid sequence such as R to K (both being positively charged) or V to I or L (all being hydrophobic) allow for a number of peptides with the similar affinity and efficacy for PAK inhibition or modulation. Thus there is expected to be a family of peptides which have certain key amino acid residues, but also other less critical amino acid residues, or additional residues which may be widely substituted.

Finally. the use of synthetic peptides is often the starting point for the development of peptide mimetics or drugs. The parts of the peptide or peptide mimetic which are in contact with PAK in 3 dimensional space so as to provide the desired biological function are critical for this purpose. Thus, a family of peptides with the same efficacy for PAK should have specific and critical moieties (e.g., carbon group, proline "kink", positive charge, or the like) located in space at the same sites, based on the structure and chemical nature of the natural substrate. Determining the structure of this family of peptides provides the preferred structure of the PAK binding/phosphorylation site and ligands which interact with said site.

To assess the specificity of PAK for the synthesized peptides, the peptides should also be tested as possible inhibitors and/or substrates for other kinases which are considered to have a regulatory role in muscle; in particular, MLCK, MAPK (Upstate Biotechnologies), ROK, and PKA (protein kinase A, active catalytic domain, Sigma). In addition, the peptides should be tested against other PAK family members including myosin I heavy chain kinase. PAK autoinhibitory peptides are expected to exhibit different activities with PAK and MAPK and PKA since their consensus sequences differ (Johnson, L. N. et al. 1996, *Cell* 85:149–158). Because both MLCK and PAK can phosphorylate smooth muscle $LC_{20}$, there may be some cross specificity within their consensus sequences, and optimization of peptide inhibitors may require peptide library screening In addition, some substrate peptides are expected to be phosphorylated by other members of the PAK family while inhibitory peptides act as inhibitors. Since there are only two amino acids within the consensus sequences of myosin I heavy chain kinase (a member of PAK family) that match with PAK, the peptides based on PAK sequence (as described above) should be less efficient with other members of the PAK family. Nevertheless, specific amino acid substitutions can be caxied out on a synthesized peptide, using methods well known in the art such as solid phase synthesis (Merrifield. 1964. *J. Am. Chem. Assoc.* 85: 2149–2154), or synthesis in homogeneous solution (Houbeniwcyl. 1987. *Methods of Organic Chemistry*, ed. E. Wansch. Vol. 15 I and II. Thieme, Stuttgart), to optimize the specificity of PAK for the peptide, and to eliminate any cross-phosphorylation with other known Ser/Thr kinases including MLCK and other members of the PAK family.

Synthesized peptides can be used to prepare PAK modulators such as PAK inhibitors where they are good substrates or competitors for PAK. Synthesized peptides may thus be tested for their utility as substrates for PAK by, for example, determining the phosphotylation kinetics of the peptides at various concentrations of PAK with $^{32}$P-ATP. The level of $^{32}$P incorporated into the peptide can be quantified following separation of the peptide from free ATP by NO-P81 paper assays or gel filtration (Sephadex G-10).

Similarly, standard kinetic assays can be perfomed to assess the effectiveness of PAK inhibitors. The more effective the peptide inhibitor is, the less phosphorylation (less $^{32}$P label) there will be of $LC_{20}$. Peptide inhibitors can also be tested against CAD and TnI. Various concentrations of peptide inhibitors canbe tested on Triton X-100 skinned smooth muscle and cardiac muscle fibers in the presence of exogenously supplied PAK to determine the optimal inhibitor concentration for inhibition of contraction. With these studies, the levels of $LC_{20}$, CAD, TnI, and any other target protein phosphorylation should preferably also be monitored.

Peptide inhibitors of PAK can be assessed in smooth muscle in vivo using different strategies. Briefly, the peptides can be perfused into reversibly permeabilized smooth muscle and alpha-toxin or β-escin skinned muscle fibers, and micro-injected into isolated myocytes. In contrast to Triton-skinned muscle fibers, these muscle preparations preserve signal transduction pathways and retain essential cytosolic mediators, making them suitable for assessment of PAK function, and hence modulator function, in vivo.

Reversible permeabilization of intact smooth muscle tissue uses high EDTA/ATP in the extracellular solution and is used frequently to load living tissue with proteins and compounds less than 100 kDa. Alpha toxin produces uniformly small holes in the plasma membrane which allow molecules under 1 kDa to enter. Because β-escin skinned fibers allow entrance of large proteins (<100 kDa), the fibers slowly run down due to slow loss of cytoplasmic proteins (including PAK) after several stimulations (Otto, B. et at 1996. *J. Physiol.* 496:317–329). This limits the number of contractions that can be carried out by a single fiber. While either of these procedures is suitable, the use of a large peptide modulator will dictate the use of the β-escin skinned fiber procedure.

For in vivo assessment of peptide inhibitors of PAK, it is necessary to activate PAK. While the exact stimulation required to activate PAK, other than PDGF in platelets and hyperosmotic shock in myocytes, is not known, various agonists known to 1) activate the Rac/Cdr42 pathway and 2) cause calcium-sensitization, ranging from PDFG to GTPγS, may activate PAK. These agonists can be pre-screened for their ability to activate PAK and/or phosphorylate its target proteins. Activation of PAK can then be determined by loading alpha-toxin skinned fibers with $^{32}$P and monitoring autophosphorylation of PAK (and incorporation of $^2$P into PAK). Following various stimulations, the fibers can be analyzed by SDS-PAGE and the level of $^{32}$P incorporated into the band migrating at the molecular weight of PAK and/or target proteins determined. PAK can also be immunoprecipitated from stimulated tissue for direct analysis, using, for example, the antibody previously used to demonstrate that PAK is present in smooth muscle (Van Eyk, J. E. et al 1998. *J. Biol. Chem.* submitted). This antibody has high affinity and specificity for PAK and is suitably used to identify the PAK band and for immunoprecipitation.

Also, with the intact preparation, intercellular calcium can be measured using the photoprotein aqueorin, which can be loaded into the smooth muscle cells. This allows measurement of calcium levels during stimulation with agonist (Rembold, C. M. et al. 1988. *Circ. Res.* 63:593–603). With either skinned fiber preparation, calcium levels are controlled by the bathing solution. This method can therefore be use to demonstrate a reduction in calcium level fluctuation in the presence of a peptide inhibitor of PAK.

As would be understood by a person of ordinary skill in the art, a variety of amino acid substitutions may be made to the above-identified peptides while preserving their structure and protein (PAK) binding activity. Conservative substitutions are described in the patent literature, as, for example, in U.S. Pat. No. 5,264,558. It is thus expected, for example, that interchange among non-polar aliphatic neutral amino acids, Gly, Ala, Pro, Val and Ile would be possible. Likewise, substitutions among the polar aliphatic neutral amino acids, Ser, Thr, Met, Asn and Gln could possibly be made. Substitutions among the charged acidic amino acids, Asp and Glu, could probably be made, as could substitutions among the charged basic amino acids, Lys and Arg. Substitutions among the aromatic amino acids, including Phe, His, Trp and Tyr would also likely be possible. These sorts of substitutions are well known to those skilled in the art. Other substitutions might well be possible. All such varants are encompassed by the scope of the invention. It would be expected that the greater the sequence similarity of the peptide to the related region of the native protein, the greater the degree of the desired biological activity.

In addition, modulators, such as inhibitors, of PAK expression or activity useful in the method of the invention include PAK specific antisense nucleic acids, ribozymes and intracellular antibodies. Antisense approaches involve the design of oligonucleotides (either DNA or RNA) that are complementary to PAK mRNA. The antisense oligonucleotides will bind to the PAK mRNA transcripts and prevent translation. Alternatively, the antisense oligonucleotide may bind to DNA of a PAK gene, such as, for example, a regulatory element. Absolute complementarity, although preferred, is not required. A sequence "complementary" to a portion of a nucleic acid, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acids Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the PAK message, e.g., the 5' untranslated sequence up to and including the AUG initiation codon, should work most efficiently at inhibiting translation. However, sequences complementary to the 3' untranslated sequences of the PAK mRNA may also be used. (Wagner, R. 1994. *Nature* 372:333). Therefore, oligonucleotides complementary to either the 5' or 3' untranslated, non-coding regions of a PAK gene could be used in an antisense approach to inhibit translation of endogenous PAK mRNA. Oligonucleotides complementary to the 5' untranslated region of the MRNA should include the complement of the AUG start codon. Antisense oligonucleotides complementary to mRNA coding regions are generally less efficient inhibitors of translation but could be used in accordance with the invention. Whether designed to hybridize to any of the aforementioned regions of PAK nucleic acid, antisense nucleic acids should be at least about six nucleotides in length, and are preferably oligonucleotides ranging from 6 to about 50 nucleotides in length. In certain embodiments, the oligonucleotide is at least about 10 nucleotides, at least about 17 nucleotides, at least about 25 nucleotides, or at least about 50 nucleotides.

Regardless of the choice of target sequence, it is preferred that in vitro studies are first performed to quantitate the ability of the antisense oligonucleotide to inhibit PAK gene expression and therefore smooth muscle contraction, or cardiac muscle calcium sensitivity. It is preferred that these studies utilize controls that distinguish between antisense gene inhibition and nonspecific biological effects of oligonucleotides. It is also preferred that these studies compare levels of the target RNA or protein with that of an internal control RNA or protein. Results obtained using the antisense oligonucleotide can be compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such agents facilitating transport across the cell membrane (see, e.g., Letsinger et al. 1989. *Proc. Natl. Acad. Sci. U.S.A.* 86:6553–6556; Lemaitre et al. 1987. *Proc. Natl. Acad. Sci. U.S.A.* 84:648–652; PCT Publication No. W088/09810, published Dec. 15, 1988).

While antisense nucleotides complementary to the PAK coding region sequence could be used, those complementary to the transcribed untranslated region are most preferred.

The antisense molecules can be delivered to smooth or cardiac muscle cells which express the PAK in vivo or in vitro. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the smooth muscle cell surface) can be administered systematically.

Since it is often difficult to achieve intracellular concentrations of the antisense molecule sufficient to suppress translation on endogenous mRNAs, a preferred approach utilizes a recombinant DNA construct in which the antisense oligonucleotide is placed under the control of a strong pol III or pol II promoter. The use of such a construct to transfect, for example, target smooth muscle cells in the patient will result in the transcription of sufficient amounts of single stranded RNAs that will form complementary base pairs with the endogenous PAK transcripts and thereby prevent translation of the PAK mRNA. For example, a vector can be introduced in vivo such that it is taken up by a smooth or cardiac muscle cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, smooth muscle or cardiac muscle cells. Such promoters can be inducible or constitutive. Such promoters include but are not limited to: the SV40 early promoter region (Bernoist et at. 1981. *Nature* 290:304–310), the promoter contained in the 31 long terminal repeat of Rous sarcoma virus (Yamamoto et al. 1980. *Cell* 22:787–797), the herpes thymidine kinase promoter (Wagner et al. 1981 *Proc. Natl. Acad. Sci. U.S.A.* 78:1441–1445), the regulatory sequences of the metallothionein gene (Brinster et al. 1982. *Nature* 296:39–42), etc. Any type of plasmid, cosmid, YAC or viral vector can be used to prepare the recombinant DNA construct which can be introduced directly into the tissue site; e.g., the gastro-intestinal tract.

Ribozyme molecules designed to catalytically cleave PAK mRNA transcripts can also be used to prevent translation of PAK mRNA and expression of PAK. (See, e.g., PCT International Publication WO 90/11364, published Oct. 4, 1990; Sarver et al. 1990. *Science* 247:1222–1225). While ribozymes that cleave mRNA at site specific recognition sequences can be used to destroy PAK mRNAs, the use of hammerhead ribozymes is preferred. Hammerhead ribozymes cleave mRNAs at locations dictated by flanking regions that form complementary base pairs with the target MRNA. The sole requirement is that the target mRNA have the following sequence of two bases: 5'-UG-3'. The construction and production of hammerhead ribozymes is well known in the art and is described more fully in Haseloffet al 1988. *Nature* 334:585–591. There are numerous potential hammerhead ribozyme cleavage sites within the nucleotide sequence of human PAK cDNA. Preferably the ribozyme is engineered so that the cleavage recognition site is located near the 5' end of the PAK mRNA; i.e., to increase efficiency and minimize the intracellular accumulation of non-functional mRNA transcripts.

Ribozymes of usefulness in the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. 1984, *Science* 224:574–578; Zaug et al. 1986. *Science* 231:470–475; Zaug et al. 1986. *Nature* 324:429–433; published International patent application No. WO 88/04300 by University Patents Inc.; Been et al. 1986. *Cell* 47:207–216). The Cech-type ribozymes have an eight base pair active site which hybridizes to a target RNA sequence whereafter cleavage of the target RNA takes place.

As in the antisense approach, the ribozymes can be composed of modified oligonucleotides (e.g., for improved stability, targeting, etc.) and should be delivered to smooth muscle or cardiac muscle cells which express a PAK in vivo. A preferred method of delivery involves using a DNA construct "encoding" the ribozyme under the control of a strong constitutive pol III or pol II promoter, so that transfected cells will produce sufficient quantities of the ribozyme to destroy endogenous PAK mRNA and inhibit translation. Because ribozymes unlike antisense molecules, are catalytic, a lower intracellular concentration is required for efficiency.

Alternatively, endogenoas PAK gene expression can be reduced by targeting deoxyribonucleotide sequences complementary to the regulatory region of the PAK gene (i.e., the PAK promoter and/or enhancers) to form triple helical structures that prevent transcription of the PAK gene in target muscle cells in the body. (See generally, Helene, C. 1991. *Anticancer Drug Des.* 6:569–84; Helene, C., et al. 1992. *Ann, N.Y. Acad. Sci.* 660:27–36; and Maher, L. J. 1992 *Bioassays* 14:807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single stand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In yet another embodiment, the antisense oligonucleotide is an α-anomeric oligonucleotide. An α-anomeric oligonucleotide forms specific doublestranded hybrids with complementary RNA in which, contrary to the usual β-units, the strands run parallel to each other (Gautier et al. 1987. Nucl. Acids Res. 15:6625–6641). The oligonucleotide is a 2'-0-methylribonucleotide (Inoue et al. 1987. Nuci. Acids Res. 15:6131–6148), or a chimeric RNA-DNA analogue (Inoue et al. 1987. FEBS Lett. 215:327–330).

In one embodiment, a PAK inhibitor is an antibody which binds to either PAK (i.e., an anti-PAK antibody) or a PAK downstream element (i.e., an anti-caldesmon antibody) to substantially block or inhibit an interaction between PAK and a PAK downstream element (i.e., blocking antibodies). Additionally, antibodies to PAK or a PAK downstream element can be produced by conventional techniques. Antibodies can be polyclonal, or more preferably, are monoclonal. Polyclonal and monoclonal antibodies can be prepared by standard techniques known in the art. For example, a mammal, (e.g., a mouse, hamster, or rabbit) can be immunized with an antigen (i.e., PAK or a PAK downstream element), for example with purified protein, recombinant protein, or peptide fragments thereof, or with a cell which expresses the antigen (e.g., expresses PAK or a PAK downstream element on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells, Such techniques are well known in the art. For example, the hybridoma technique originally developed by Kohler and Milstein (1975. *Nature* 256:495–497) as well as other techniques such as the human B-cell hybridoma technique (Kozbar et al. 1983. *Immunol. Today* 4:72), and the EBV-hybridoma technique to produce human monoclonal antibodies (Cole et al. 1985. *Monoclonal Antibodies in Cancer Therapy* Allen R. Bliss, Inc., pages 77–96) can be used. Hybridoma cells can be screened immunochemically for production of antibodies specifically reactive with the antigen and monoclonal antibodies isolated.

Another method of generating specific antibodies, or antibody fragments, reactive against PAK or a PAK downstream element is to screen expression libraries encoding immunoglobulin genes, or portions thereof, expressed in bacteria with the antigen (or a portion thereof). For example, complete Fab fragments, $V_H$ regions, $F_V$ regions and single chain antibodies can be expressed in bacteria using phage expression libraries. See for example Ward et al. 1989. *Nature* 341:544–546; Huse et al 1989. *Science* 246:1275–1281; and McCafferty et al. 1990. *Nature* 348:552–554. Alternatively, the SCID-hu mouse can be used to produce antibodies, or fragments thereof.

As used herein, the term "antibody" is intended to include fragments thereof which retain a desired functional property, e.g., the ability to inhibit an interaction between PAK and a PAK downstream element. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments.

The term "antibody" is filter intended to include derivatives thereof which retain a desired functional property, e.g., the ability to inhibit an interaction between PAK and a PAK downstream element. Antibody derivatives include chimeric molecules, humanized molecules, molecules with reduced effector functions and bispecific molecules. An antibody, or fragment thereof, produced in a non-human subject can be recognized to varying degrees as foreign when the antibody is administered to a human subject and an immune response against the antibody may be generated in the subject. One approach for minimizing or eliminating this problem is to produce chimeric or humanized antibody derivatives, i.e., antibody molecules comprising portions which are derived from non-human antibodies and portions which are derived from human antibodies. Chimeric antibody molecules can include, for example, the variable region from an antibody of a mouse, rat, or other species, with human constant regions. A variety of approaches for making chimeric antibodies have been described. See, for example, Morrison et al. 1985. *Proc. Natl. Acad. Sci. U.S.A*. 81:6851; Takeda et al. 1985. *Nature* 314:452: Cabilly et al. U.S. Pat. No. 4,816, 567; Boss et al. U.S. Pat. No. 4,816,397; Tanaguchi et al. European Patent Publication EP171496; European Patent Publication 0173494, United Kingdom Patent GB 2177096B. In a further modification, humanized antibodies have only the hypervariable domains of the variable region of non-human origin and have other parts of the variable region of the antibody, especially the conserved framework regions of the antigen-binding domain, of human origin. Such humanized antibodies can be made by any of several techniques known in the art, (e.g., Teng et al. 1983. *Proc. Natl. Acad. Sci. U.S.A*. 80: 7308–7312; Kozbor et al. 1983. *Immunology Today* 4:727; Olsson et al. 1982. *Meth. Enymol*. 92:3–16), and are preferably made according to the teachings of PCT Publication WO92/06193 or EP 0239400. Humanized antibodies can be commercially produced by, for example, Scotgen Limited 2 Holly Road, Twickenham, Middlesex, Great Britain.

For use therapeutically, it is also preferred that an antibody preparation be unable to fix complement or induce other effector functions. Complement fixation can be prevented by deletion of the Fc portion of the antibody, by using an antibody isotype which is not capable of fixing complement, or, less preferably, by using a complement fixing antibody in conjunction with a drug which inhibits complement fixation. Alternatively, amino acid residues within the Fc region which are important for activating complement (see e.g., Tan et al. 1990. *Proc. Natl. Acad. Sci. USA* 87:162–166; Duncan et al. 1988. *Nature* 332;738–740) can be mutated to reduce or eliminate the complement-activating ability of an intact antibody. Likewise, amino acids residues within the Fc region which are important for binding of the Fc region to Fc receptors (see e.g., Canfield, S. M. et al. 1991. *J. Exp. Med*. 173:1483–1491; Lumd, J. et al. 1991. *J. Immunol*. 147:2657–2662) can also be mutated to reduce or eliminate Fc receptor binding if an intact antibody is to be used.

An antibody which binds to PAK or a PAK downstream element can be assessed for blocking or inhibitory activity by conventional techniques. For example, the ability of the antibody to block phosphorylation of caldesmon can be determined.

PAK potentiators are those agents capable of potentiating the activity of a PAK kinase, PAK modulating agents including inhibitors and potentiators can be readily identified using the screening methods described below and adapted to therapeutic uses.

PAK modulating agents can be used alone or in conjunction with other agents which effect PAK kinase activity. For example, PAK modulating agents can be used with calcium to further enhance or increase contraction of a smooth or cardiac muscle, e.g., involved in states desired to be treated. In some embodiments, the smooth or cardiac muscle contraction involved in the method is considered to be calcium sensitive and the PAK modulating agent(s) of the present invention enhance the calcium's ability to induce or modulate smooth or cardiac muscle contraction, e.g., the enhancement can be observed by determining the force per concentration of calcium.

Another aspect of the invention pertains to a method of treating a subject having a state characterized by smooth muscle contraction. The method involves administering to a subject a therapeutically effective amount of a PAK modulating agent, e.g., a PAK inhibitor, such that treatment of the state characterized by smooth muscle contraction occurs. In one embodiment, the state is characterized by the contraction of smooth muscle having a high basal tone. In another embodiment, the state characterized by the contraction of smooth muscle involves a state characterized by abnormal or inappropriate contraction of smooth muscle In yet another embodiment, the state characterized by the contraction of smooth muscle involves abnormal or inappropriate relaxation of smooth muscle. In yet another embodiment, the treatment of the state involves the reduction or inhibition of inappropriate smooth muscle contraction. Examples of states include hypertension, asthma, irritable bowel syndrome, incontinence, and menstrual cramps.

Another aspect of the invention pertains to a method of treating a subject having a state characterized by cardiac contractile dysfunction. For example, the state characterized by cardiac contractile dysfunction can be a state having decreased cardiac contraction in response to calcium (decreased calcium-sensitivity). The method involves administering to a subject a therapeutically effective amount of a PAK modulating agent, e.g., a PAK stimulator, such that increased calcium sensitivity occurs. As well, the method also provides for the administration of PAK or the catalytic domain of PAK directly to heart muscle. In another embodiment, the state is characterized by increased cardiac contraction in response to calcium (increased calcium-sensitivity). The method involves administering to a subject a therapeutically effective amount of a PAK modulating agent, e.g., a PAK inhibitor, such that decreased calcium-sensitivity occurs. In yet another embodiment, the state characterized by the contraction of cardiac muscle involves abnormal or inappropriate contraction or relaxation of cardiac muscle. In yet another embodiment, the treatment of the state involves the modulation of inappropriate cardiac contraction or relaxation. Examples of characterized by cardiac contractile dysfunction include myocardial stunning, myocardial infarction, myocardial myopathies and heart failure, Clinical conditions which require inotropic intervention can use modulation of PAK and its effect on Ca-sensitivity of cardiac muscle.

As used herein, the term "state" is art recognized and includes a disorder, disease or state characterized by the contraction of smooth or cardiac muscle.

As used herein, the term "hypertension" is art recognized and includes the state in which excessive smooth muscle contraction of a blood vessel occurs which results in hypertension in a subject.

As used herein, the term "asthma" is art recognized and includes the state in which excessive smooth muscle contraction of the airways in the lungs of a subject occurs.

As used herein, the term "incontinence" is art recognized and includes the state in which excessive smooth muscle contraction of the urinary tract occurs.

As used herein, the term "irritable bowel syndrome" is art recognized and includes the state in which excessive smooth muscle contraction of the gastro-intestinal tract occurs.

As used herein, the term "menstrual cramps" is art recognized and includes the state in which excessive smooth muscle contraction of the uterus occurs.

As used herein, the term "cardiac contractile dysfunction" is art recognized and includes the states in which myocardial contractility is either insufficient or excessive.

For the purposes of this invention, the term "therapeutically effective amount" includes an amount effective, at dosages and for periods of time necessary, to achieve the desired level of smooth or cardiac muscle contraction. A therapeutically effective amount of a PAK modulating agent, e.g., a PAK inhibitor, may vary according to factors such as the disease state, age, and weight of the individual, and the ability of the PAK modulating agent to elicit a desired level of muscle contraction or calcium sensitivity in the subject. Dosage regimens may be adjusted to provide the optimum therapeutic response. A therapeutically effective amount is also one in which any toxic or detrimental effects of the PAK modulating agent are outweighed by the therapeutically beneficial effects. It is to be noted that dosage values may vary with the severity of the state to be alleviated. It is to be fiber understood that for any particular subject, specific dosage regimens should be adjusted over time according to the individual need and the professional judgment of the person administering or supervising the administration of the PAK modulating agents A PAK modulating agent, e.g., PAK inhibitor, can be administered to a subject by a variety of methods known in the art. The PAK modulating agent can be provided in a manner such that it can be taken up by the cell or in a manner such that it can be converted to a form that can be readily taken up by the cell. In various embodiments, the PAK modulating agent is administered in a formulation suitable for intravenous, intraperitoneal, subcutaneous, intramuscular, intravaginal, topical, transdermal or oral administration. In a preferred embodiment, the PAK modulating agent is administered in a time release formulation (also referred to as a sustained-release formulation), for example in a composition which includes a slow release polymer, or a composition suitable for depot injection. The PAK modulating agent can be prepared with carriers that will protect the inhibitor against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthocaters, polylactic acid and polylactic, polyglycolic copolymers (PLG). Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. Particularly preferred formulations include controlled-release compositions such as arm known in the art for the administration of leuprolide, e.g., microcapsules (U.S. Pat. Nos. 4,652,441 and 4,917,893), injectable formulations (U.S. Pat. No. 4,849,228), lactic acid-glycolic acid copolymers useful in making microcapsules or injectable formulations (U.S. Pat. Nos. 4,677,191 and 4,728,721), and sustained-release compositions for water-soluble polypeptides (U.S. Pat. No. 4,675,189).

When appropriately formulated, a PAK modulating agent may be orally administered, for example, with an inert diluent or an assimilable edible carrier. The PAK modulating agent may also be enclosed in a hard or soft shell gelatin capsule, compressed into tablets, or incorporated directly into the subject's diet. For oral therapeutic administration, the PAK modulating agent may be incorporated with excipients and used in the form of ingestible tablets, buccal tablets, troches, capsules, elixirs, suspensions, syrups, wafers, and the like. The percentage of the PAK modulating agent in the compositions and preparations may, of course, be varied. The amount of the PAK modulating agent in such therapeutically useful compositions is such that a suitable dosage will be obtained.

To administer a PAK modulating agent by other than parenteral administration, it may be necessary to coat the compound with, or co-administer the compound with, a material to prevent its inactivation. For example, the PAK modulating agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. 1984. *J. Neuroinmunol.* 7:27). Pharmaceutically acceptable carriers include sterile aqueous solutions or dispersions and sterile powders for the extemporaneous preparation of sterile injectable solutions or dispersion The use of such media and agents for pharmaceutically active substances is well known in the axt. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

Sterile injectable solutions can be prepared by incorporating the PAK modulating agent in the required amount in an appropriate solvent with one or a combination of ingredients enumerated above, as required, followed by filtered sterilization. Generally, dispersions are prepared by incorporating the PAK modulating agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Dosage regimens may be adjusted to provide the optimun therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the PAK modulating agent and the particular therapeutic effect to be achieved, and (b) the limitations inherent in the art of compounding such a PAK modulating agent for the treatment of states described herein.

In yet another embodiment, the invention provides a method for identifying PAK modulating agents. For example, modulating agents which are inhibitors, or alternatively, stimulators, of PAK kinase activity can be identified. The method involves providing an indicator composition comprising a PAK protein having PAK kinase activity, contacting the indicator composition with a test agent, and determining the effect of the test agent on PAK kinase activity in the indicator composition to thereby identify a compound that modulates the kinase activity of a PAK protein. In a prefer embodiment, the screening assay identifies agents that modulate the kinase activity of a PAK protein, for example, peptides or peptide mimetics. A statistically significant change, such as a decrease or an increase, in the level of PAK kinase activity in the presence of the test agent (relative to what is detected in the absence of the test agent) is indicative of the test agent being a PAK modulating agent.

Morgan and co-workers (Morgan et al. 1989. In: *Annual Reports in Medicinal Chemistry*. Ed.: Vinick, F. J. Academic Press, San Diego, Calif., pp. 243–252.) define peptide mimetics as "structures which serve as appropriate substitutes for peptides in interactions with receptors and enzymes. The mimetic must possess not only affinity but also efficacy and substrate function. As used herein, the term "peptide mimetic" is used in a manner consistent with the above art-recognized definition. That is, a peptide mimetic exhibits function(s) of a particular peptide, without restriction of structure. Peptide mimetics of the invention, e.g., analogues of structural motifs such as the PAK autophosphorylation site or the substrate binding site of PAK, may include amino acid residues or other chemical moieties which provide the desired functional characteristics.

As used herein, the term "indicator composition" is intended to include any composition that can be used to screen and identify PAK modulating agents. The indicator composition can be, for example, a smooth muscle cell, a cardiac myocyte, a smooth muscle cell or cardiac muscle cell extract, or a detergent-skinned smooth or cardiac muscle fiber bundle system. Methods for the preparation of intact smooth muscle cells or extracts from such cells are well known in the art and previously described (Glukhova et al. 1987. *Tissue Cell* 19:657–63; Childs et al. 1992. *J. Biol. Chem.* 267:22853–9, 1992; White et al. 1996. *J. Biol. Chem.* 271:15008–17). Methods for preparing Triton-skinned smooth and cardiac muscle fiber bundles are also Imown in the art (Strauss et al. 1992. *Am. J. Physiol.* 262:1437–45; Van Eyk, J. E. et al. 1998. *Circ. Res.* 82:261–271). Bovine cardiac and rabbit skeletal troponin can be purified as outlined in Ingraham R. H. et al., 1988. *Biochemistry* 27:5891–5898.

As used herein, the language "modulates PAK kinase activity" is art-recognized and is intended to include the capacity to inhibit or stimulate PAK kinase activity, e.g., the ability of the PAK kinase to phosphorylate its substrates. The modulation can be complete inhibitor or partial inhibition. The modulation of PAK kinase activity include, modulation to the extent necessary or sufficient to treat the states described herein.

As used herein the term "test agent" is intended to include an agent that modulates the kinase activity of PAK. Such agents can be, for example, a drug, an antibiotic, an enzyme, a chemical compound, a mixture of chemical compounds, a biological macromolecule, and analogues thereof.

As used herein the term "PAK protein" is intended to include a protein that belongs in the family of PAK serine/threonine protein kinases and has the ability to induce smooth muscle contraction, e.g., in the absence of calcium, or to change the calcium sensitivity of cardiac muscle. These include mammalian isoform identified, e.g., PAK1, PAK2, PAK3, or lower eucaryotic isoforms, such as the yeast Ste20 (Leberter et al., EMBO J. 11:4805–13, 1992) or the Dictyostelium single-headed myosin I heavy chain kinases (Wu et al., J. Biol. Chem. 271:31787–90, 1996).

In one embodiment, PAK kinase activity is assessed by measuring phosphorylation of the caldesmon protein. In another embodiment, PAK kinase activity is assessed by measuring phosphorylation of the myosin light chain ($LC_{20}$). In still a further embodiment, PAK kinase activity is assessed by measuring phosphorylation of the calponin protein. In further embodiments, PAK kinase activity is assessed by measuring phosphorylation of TnI or any target protein in cardiac muscle. Several methods are known in the art and readily available for determining the activity of candidate PAK inhibitors or stimulators against PAK kinase on intact cells, cell extracts or skinned smooth muscle and cardiac muscle fibers. Phosphorylation of the PAK kinase cellular substrates (e.g., caldesmon, myosin light chain ($LC_{20}$), calponin, TnI) can be measured using antiphosphoserine antibodies or phosphopeptide fingerprints, methods well known in the art and described in the "Examples" section In many drug screening programs which test libraries of modulating agents and natural extracts, high throughput assays are desirable in order to maximize the number of modulating agents surveyed in a given period of time. Assays which are performed in cell-free systems, such as may be derived with smooth muscle and cardiac muscle cell extracts, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focussed primarily on the effect of the test agent on the PAK kinase as may be manifest in an alteration of phosphorylation of downstream elements.

The efficacy of the test agent can be assessed by generating dose response curves from data obtained using various concentrations of the test modulating agent. Moreover, a control assay can also be performed to provide a baseline for comparison. In the control assay, the indicator composition comprising the PAK kinase is incubated in the absence of a test agent.

The present invention is further illustrated by the following example, which should not be construed as limiting. The contents of all references, pending patent applications, and published patents, cited throughout this application (including the "Background" Section) are hereby expressly incorporated by reference.

EXAMPLE

Methods

Protein Preparations

Intact smooth muscle myosin, $LC_{20}$, myosin light chain kinase (MLCK) and caldesmon were purified from chicken gizzard (Hathaway, D. R. et al. 1983. *Anal. Biochem.* 135:37–43; Ikebe, M. et al. 1985. *J. Biol. Chem.* 260:10027–10031; Bretscher, A. 1984. *J. Biol. Chem.* 259:12873–12880) while PAK3 was isolated from rat brain (Wu, C. et al. 1995. *J. Biol. Chem.* 270:25070–25078).

Recombinant caldesmon fragments (CAD39 and CAD40) were prepared and purified as previously described (Novy, R. E. et al. 1993. *Cell Motil. Cytosk.* 26:248–261). Recombinant Cdc42 and Rac1 were expressed and purified as described in Manser, E. et al. (1994. *Nature* 367:40–46). Plasmid pGST-mPAK3 encoding mouse fibroblast mPAK3 fused to GST in pGEX-KG was expressed and the fiusion protein purified according to Manser, E. et al. (1994. *Nature* 367:40–46). Plasmid pDK-mPAK3$^{K297R}$ encoding an inactive mPAK3 mutant with lysine amino acid residue 297 was mutated to argine 297 (mPAK3$^{K297R}$ cDNA) and fused to GST by subjoining a BamH1 fragment of PDK-mPAK3$^{K297R}$ into pGEX4T3. The GST-mPAK3 fusion proteins were expressed in *E. coli*. The catalytic subunit of recombinant ROK (Rho-kinase) was expressed as a GST fusion protein in baculovirus (GST-ROK; 5). All recombinant kinases were purified on a glutathione-Sepharose affinity column (Amersham Pharmacia), concentrated (Amicon) and dialyzed against 10 mM imidazole, pH 7.0. As reported previously (Bagrodia, S. et al. 1995. *J. Biol. Chem.* 270:27995–27998), GST-mPAK3 is susceptible to degradation, leading to different activities for each preparation. In order to ensure consistency, activities of the various GST-mPAK3 preparations were standardized against myelin basic protein phosphoiylation. GST-mPAK was used in the skinned fiber assay within 4 days but could maintain sufficient activity for in vitro phosphorylation analysis if stored frozen in 50% glycerol. Various preparations of GST-mPAK3 (~0.5 to 5 µg/ml of active GST-mPAK3) were able to induce $Ca^{2+}$-independent contractions in skinned smooth muscle fibers ranging from 26.1 to 80.9% of $Ca^{2+}$-dependent contraction.

Preparation of Detergent-skinned Smooth Muscle Fibers

Triton-X100 skinned fibers from adult guinea pig taenia coli were prepared as previously described (Strauss, J. D. et al. 1992. *Am. J. Physiol.* 262:C1437–1445; Strauss, J. D. et al. 1993. *Methods: A Companion to Methods in Enznology* 5,281–290). The skinned fiber bundles were stored at −20° C. in a solution containing 50% glycerol (v/v), 4 mM EGTA, 1 mM sodium azide, 7.5 mM ATP, and 20 mM imidazole, pH 6.7 and used within one month. Thin fiber bundles (~100 µm in diameter) were mounted on an AME 801, Sensonor, Norway) force transducer for analysis (26,27). "Relaxing" solution consisted of 10 mM magnesium chloride, 1 mM sodium azide, 7.5 mM disodium ATP, 4 mM EGTA, and 20 mM imidazole (pH 6.7), 10 mM sodium phosphocreatine and 10 U/ml creatine phosphokinase (ionic strength of 110 mM, 2mM free $Mg^{2+}$, and 7.2 mM MgATIP). "Contracting" solution consisted of relaxing solution supplemented to 0.1 mM calmodulin and 4.0 mM calcium chloride (pCa=4.3). The solutions used to bathe the fibers contained either GST-mPAK3, GST-mPAK3$^{K297R}$ GST-ROK or an equivalent amount of 10 mM imidazole buffer used in the final dialysis during preparation of PAK and ROK.

Mechanical Measurements of Smooth Muscle

Small smooth muscle fiber bundles (5.0 mm in length and 100–200 µm in diameter) were dissected from the muscle strip and mounted for isometric force measurements as previously described (Strauss, et al., 1992). To induce contraction, the strips were incubated in the contracting buffer containing $Ca^{2+}$(pCa=4.5) and 1 µM calmodulin. Fibers generated between 0.5 and 2.5 milliNewtons (mN) of force within 2 to 10 minutes ($1.5 \times 10^5$ N/M$^2$). To study the effect of exogenous GST-mPAK3 and GST-mPAK3$^{K297R}$ on force generation of the skinned fibers, ~5 µ/ml (55 nM) of each protein was included in the relaxing buffer. To demonstrate the phosphorylation of target protein in skinned smooth muscle fibers with GST-mPAK3, skinned fibers were incubated in the relaxation buffer containing either GST-mPAK3 or GST-mPAK3$^{KR297}$ and 1 mM $\gamma^{32}$P[ATP] (1 mCi per ml). After 60 min of incubation at 25° C., the fiber was washed with the relaxation buffer to remove ATP. The washed fiber was analyzed by 2-dimensional isoelectric focusing/SDS-PAGE as described (Nixon, G. F. et al. 1995. *J. Physiol.* 487:283–289), 1D SDS-PAGE, or 1D isoelectric focusing on a gel (Strauss, J. D. et al. 1992). Subsequently, autoradiography and corresponding western blot analyses indicated that caldesmon and desmin were phosphorylated.

Cardiac Skinned Fiber Bundle Experiments

Hearts from rat and dissected trabecula were placed in ice cold relaxing buffer containing 0.1 mmol/l EGTA, 2 mmol/l $Mg^{2+}$, 79.2 mmol/l potassium chloride, 5.0 mmol/l MGATP$^{2-}$, 12 mmol/l creatine phosphate, and 20 mmol/l MOPS, pH 7.0 (ionic strength, 150 mmol/l), plus a protease inhibitor cocktail (50 µmol/l phenylmethylsulfonyl fluoride, 3.6 µmol/l leupeptin, and 2.1 µmol/l pepstatin A). Fiber bundles (≈100 µm in diameter) from the trabeculae were glued to a force transducer (AME 801, Sensonor, Norway) at one end and to a fixed post attached to a micromanipulator. The fibers were skinned in relaxing buffer containing 10 IU/ml creatine kinase and 1% Triton X-100 for 30 to 45 minutes. The fibers were transferred to relaxing buffer containing 10 IU/ml creatine kinase, and the sarcomere lengths were set at 2.2 µm on the basis of the laser diffraction pattern. Isometric pCa-force relations were determined by bating the skinned fiber bundles sequentially in solutions (10 mmol/l EGTA, 2 mmol/l $Mg^{2+}$, 79.2 mmol/l potassium chloride, 5.0 mmol/l MGATP$^{2-}$, 12 mmol/l creatine phosphate, 10 IU/ml creatine kinase, and 20 mmol/l MOPS, pH 7.0 [ionic strength, 150 mmol/l]) that contained increasing concentrations of calcium chloride to achieve pCa values from 8.0 to 4.5. Fibers were contracted at pCa 4.3 (maximum response), 5.5, or 6.25 (submaximal calcium concentration) and relaxed several times, then placed in a solution containing ~5 µg/ml GST-mPAK (~55 nM) at various calcium concentrations.

Gel Overlay Assay

Gel overlay assay was performed as outlined in Manser, E. et al. 1996 (*Methods in Ezymology* 256:215–227). Intact and skimmed smooth muscle (ileum, aorta) and cardiac muscle samples were analyzed by 10% SDS-PAGE supplemented with 10% glycerol, 5 mM magnesium chloride and 1 mM dithiothreitol. Following transfer to nitrocellulose the proteins were denatured by incubating in a solution of 6M guanidine HCl, 50 mM zinc chloride, 5mM magnesium chloride, 25 mM MES pH 6.5 and 0.05% Triton X-100 (30 min at 4° C.), then renatured by incubating three times with 50 mM sodium chloride, 2.5 mM dithiothreitol, 25 mM MES, pH 6.5, 1.25 mM magnesium chloride, 50 mM zinc chloride, 1% bovine serum albumin and 0.05% Triton X-100 (2 hours at 4° C.). Purified recombinant human Cdc42 and Rac1 were labelled with S$^{35}$-GTPγS prior to probing of the nitrocellulose blots.

Protein Phosphorylation

In vitro phosphorylation of intact smooth, skeletal, cardiac, and Dictyostelium myosin and isolated LC$_{20}$, caldesmon, and caldesmon fragments, and cardiac and skeletal Tn were carried out at 25° C. in 10 mM Tris, pH 7.0, 50 mM sodium chloride, 1 mM [γ$^{32}$P]ATP ($5 \times 10^5$ cpm per nmol) or at 37° C. in the same buffer except containing 150 mM sodium chloride. Aliquots of the reaction mixture were analyzed for protein phosphorylation using Whatman P81 paper and SDS-gel electrophoresis/autoradiography as previously described (Childs, T. J. et al. 1992. *J. Biol. Chem.*

267:22853–22859). In the case of cardiac axid skeletal Tn, the three Tn subunits (TnI, TnT, and TnC) were separated by reversed phase HPLC. The individual subunits were analyzed for incorporation of $^{32}$P (i.e., phosphorylation by PAK) by SDS-PAGE and autoradiography and direct counting.

Phosphorylated amino acids wee identified by thin-layer electrophoresis after partial hydrolysis of the phosphorylated proteins in 6 N hydrochloric acid as previously described (Childs, T. J. et al. 1992. *J. Biol. Chem.* 267:22853–22859; Mak, A. S. et al. 1991. *J. Biol. Chem.* 266:19971–19975; Mak, A. S. et al. 1991. *J. Biol. Chem.* 266:6678–6681). Two-dimensional tryptic peptide maps were produced as piously described (Childs, T. J. et al. 1992. *J. Biol. Chem.* 267:22853–22859; Mak, A. S. et al. 1991. *J. Biol. Chem.* 266:19971–19975; Mak, A. S. et al. 1991. *J. Biol. Chem.* 266:6678–6681).

GST-mPAK3 and GST-ROK Phosphorylation Assay in Skinned Smooth Muscle Fibers

Smooth muscle skinned fibers mounted on a "U-shaped" pin were incubated at 25° C. under various conditions using the same conditions as in the skinned fiber assays, except, when required, assay buffers contained 1 mM [$\gamma^{32}$P]-ATP (0.25 mCi per ml) instead of 7.2 mM ATP. After 90 min incubation, fibers were submerged in ice cold 15% trichloroacetic acid and 2 mM inorganic phosphate followed by acetone, to inactivate the kinase/phosphatases. This ensures preservation of the phosphorylation levels. Fibers were stored at −20° C. until analysis. When required, autoradiographs were prepared from the same blots used for western blotting. Phosphoimages of the blots were developed using the Storm phosphorimager 820 (Molecular Dynamics, Sunnyvale, Calif.) or directly on film (X-Omat Blue XB-1, Kodak).

Actin-Tropomyosin Binding Assay

To quantitate the amount of smooth muscle caldesmnon and smooth muscle tropomyosin bound to the skeletal actin thin filament (>95% amino acid homology to smooth muscle actin), centrifugation studies were carried out in binding buffer consisting of 20 mM Tris-HCl pH 7.2, 10 mM KCl, 5 mM MgCl$_2$ and 1 mM DTT. The concentration of actin was 5 nmole/200 μl (~25 μM) and the mole ratio of actin to tropomyosin was 7:2. Increasing quantities of unphosphorylated or phosphorylated caldesmon were added to the actin-tropomyosin mixture. Protein concentrations were determined by the Lowry method or by absorbance at 280 nm. Samples were spun for 30 min at approximately 95,000 rpm, resulting in the pelleting of over 95% of the actin. The obtained pellets were dissolved in 100 μl of 0.05% aqueous trifluroacefic acid (TFA) and injected on a Zorbax C8 SB300 reversed-phase column (4.6 mm×250 mm) on a Varian HPLC system (Star series). The various proteins were eluted using a 2% B/min linear A/B gradient with a 5 min initial isocratic hold, where solvent A is 0.05% aqueous TFA and solvent B is 0.05% TFA in acetonitrile. The flow rate was 1 ml/min. The peak areas were determined at 210 nm and converted to nanomoles using a standard curve obtained for each protein. The amount of protein pelleted in the absence of actin was subtracted from the amount pelleted in the presence of actin. The experiments were done in triplicate and the standard deviation calculated.

Actin-Tropomyosin Activated ATPase Activity of Smooth Muscle Subfragment 1 (S1)

Reactions consisted of 10 μM actin, 2 μM tropomyosin, 0.5 μM S1, and variable concentrations of unphosphorylated and phosphorylated caldesmon. The buffer contained 40 mM Tris-HCl pH 7.8, 50 mM KCl, 5 mM MgCl$_2$, 1 mM DTT at 37° C. Reactions were performed in a 96 well microtitre plate, triggered by the addition of 4 mM ATP. The phosphate assay was performed according to the method of Chifflet, S. et al. 1988. (*Anal. Biochem.* 168:1–4). Briefly, reactions were terminated by the addition of an equal volume (100 μL) of reagent which contained 6% (w/v) SDS, 3% (w/v) ascorbic acid, 1M HCl, 0.5% (w/v) ammonium molybdate. The mixture was incubated for 5 minutes prior to the addition of a second reagent which contained 2% sodium citrate, 2% sodium m-arsenite, and 2% acetic acid. Blue colour developed quickly over 5 minutes, Micmotitre plates were read at 650 nm on an E-max ELISA plate reader (Molecular Dynamics, Sunnyvale Calif.). Phosphate was determined by comparing experimental values to standard phosphate values obtained through dilution of phosphate-buffered saline (PBS).

Western Blot Analyses 10 and 12% SDS-PAGE and western blot analysis were carried out as described (Van Eyk, J. et al. 1998. *Cir. Res.* 82:261–271). Preparations of skinned muscle fibers as described above were homogenized in sample buffer prior to analysis. Detection of the PAK homologue in smooth muscle was achieved using an antibody raised against a synthetic peptide corresponding to 13 residues at the N-terminal end of mouse fibroblast mPAK3 (NT3 MAb, gift from S. Pelech, Kinetek Inc., Vancouver, Canada, dilution 1:200). Caldesmon, desmin and LC$_{20}$ were detected using the following antibodies: clone hHCD (dilution 1:2000, Sigma), clone DEU-10 (dilution 1:100, Sigma) and clone MY-21 (dilution 1:200, Sigma), respectively. For quantification of LC$_{20}$ phosphorylation, skinned muscle fibers (2–3 fibers/lane) were subjected to one-dimensional isoelectric focusing (Strauss, J. D. et al. 1992. *Am. J. Physiol.* 262:C1437–1445), separating unphosphorylated LC$_{20}$ from mono- and di-phosphorylated LC$_{20}$. The ratio of phosphorylated to total LC$_{20}$ was quantified by densitometry (Sigma Gel).

Visualization of blots was carried out as follows. After the nitrocellulose membrane (blot) was blocked, it was washed several times in PBS-T to remove traces of blocking solution. The blot was then probed with primary antibody and it was rocked slowly for one hour. Antibody was prepared in PBS-T with 0.5% blocking solution (Boehringer Mannheim chemiluminescence blotting substrate POD) and an antibody concentration of between 1 to 5 μg/ml was used. Primary antibody was removed and the blot was washed several times in PBS-T. Next, a secondary antibody was added and the solution rocked slowly for one hour. Secondary antibody was prepared in a similar fashion as was the primary antibody. Secondary antibody was then removed and the blot washed several times in PBS-T. After the final wash, 0.1 M Tris-HCl, pH 9.5 was added to the blot and it was rocked slowly for 5 min. The Tris-HCl was removed and 1.0 ml of chemiluminescence reagent (CDP-STAR chemiluminescence reagent, NEN Life Science Products) was added to the blot, so as to evenly cover the blot, which was then kept still for 5 min. The blot was removed with forceps and excess chemiluminescence reagent was removed from the blot by wiping on the side of the container. After the excess chemiluminescence reagent was removed, the blot was placed face down on waxed paper and wrapped, ensuring that no air bubbles were present between the blot and the waxed paper. The blot was then exposed to film.

Results

Smooth Muscle

Figure 1:
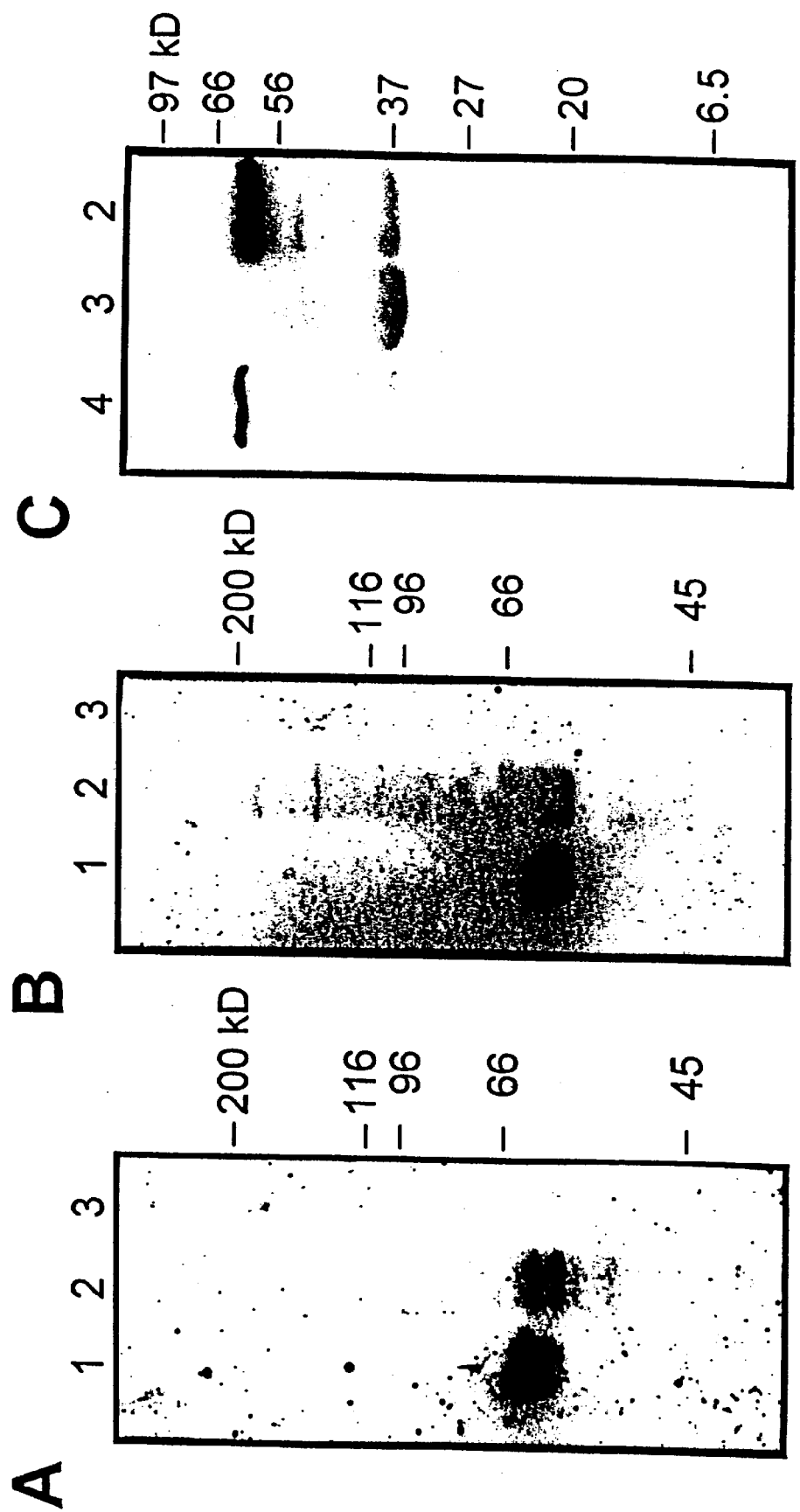
FIGS. 1A and 1B show recombinant Cdc42 (1A) or Rac1 (1B), labelled with [$^{35}$S]GTPγS, used in overlay assays of purified brain mPAK3 (1) and either intact (2) or Triton X-100 skinned (3) guinea pig taenia coli smooth muscle fibers.
FIG. 1C shows a western blot of a 12% SDS-polyacrylamide gel of intact (2) or skinned (3) guinea pig taenia coli and intact rat aorta (4) using an antibody raised against a synthetic peptide corresponding to residues 1–13 of mouse fibroblast mPAK3 (clone 3NT).

Overlay assays with Cdc42 and Rac1 indicate that [$^{35}$S] GTPγS-Cdc42 bound to bands of 62 and 65 kDa in extracts of guinea pig taenia coli smooth muscle while [$^{35}$S]GTPγS-Rac1 detected a single band of 62 kDa (FIGS. 1A & B). An antibody raised against the N-terminal 13 amino acid residues of mouse fibroblast mPAK3 reacted with a protein of 62 kDa in guinea pig smooth muscle and a protein of the same molecular mass in rat aorta (FIG. 1C). These results indicate that smooth muscle contains one, and possibly two, PAK isoforms FIG. 1A). PAK was absent from Triton-skinned smooth muscle fibers (FIGS. 1A & B) suggesting that, like ROK (Kureishi, Y. et al. 1997. *J. Biol. Chem.* 272:12257–12260), PAK is either a cytoplasmic or membrane-bound enzyme.

Figure 2A:
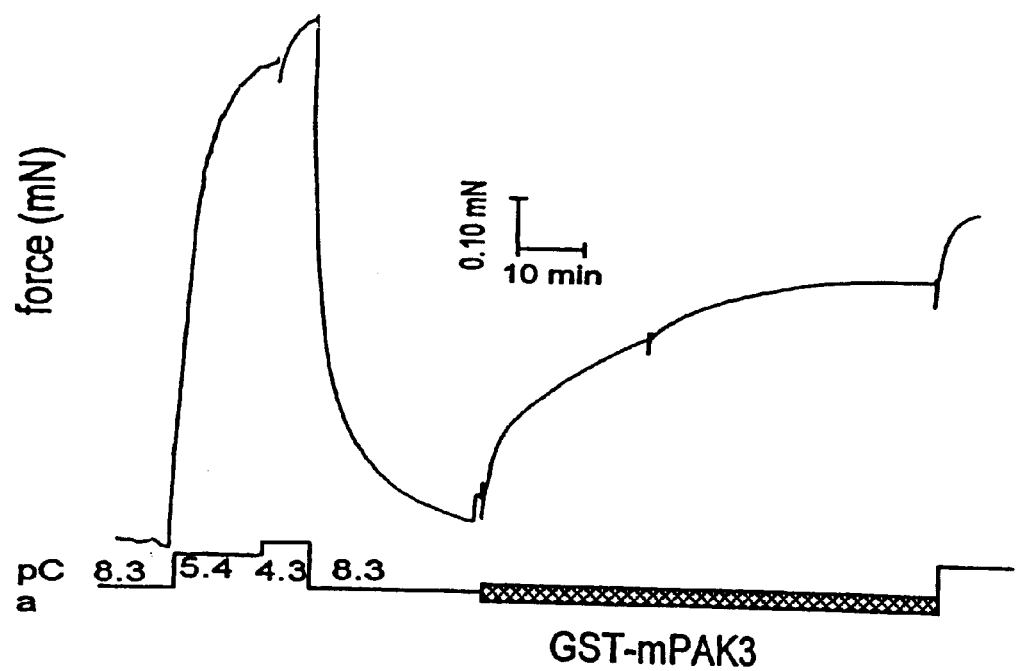
FIGS. 2A and 2B show typical isometric force tracings of Triton X-100 skinned guinea pig taenia coli fibers in the presence of constitutively active GST-mPAK3 (2A), or the inactive mutant GST-mPAK3$^{K297R}$ (2B). Fibers were contracted (pCa 5.6 and/or 4.3) and relaxed (pCa 8.3) subsequent to incubation with GST-mPAK3 (bar) at pCa 8.3.
Figure 2B:
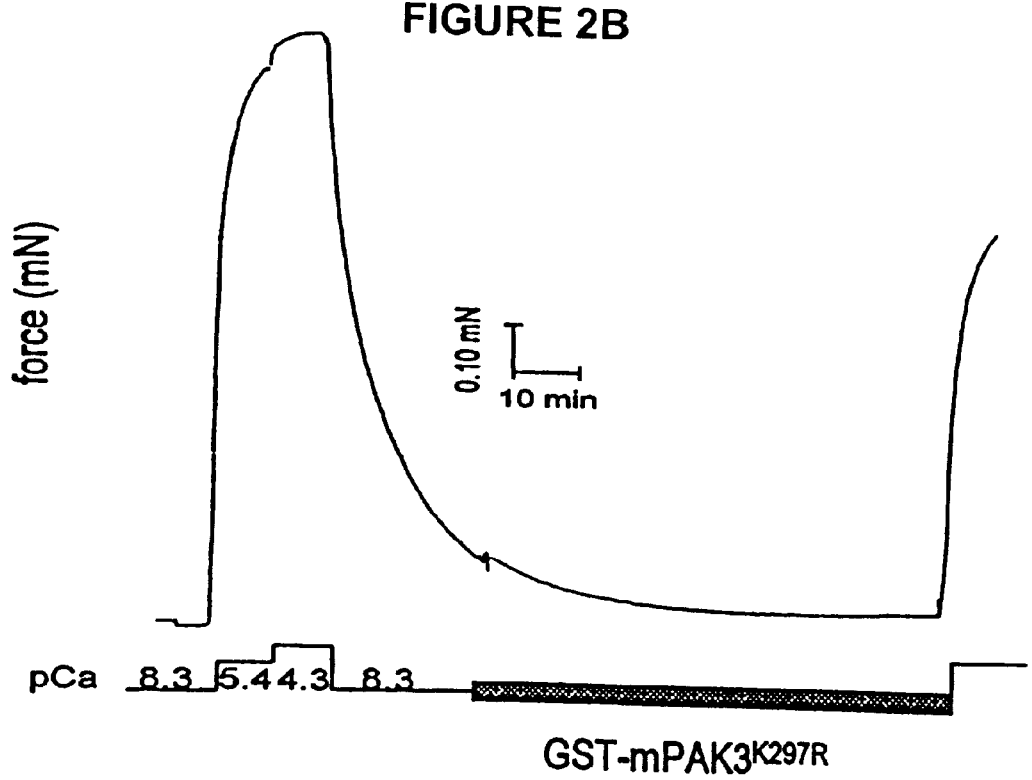

Triton-skinned guinea pig taenia coli smooth muscle fibs were induced to contract in a $Ca^{2+}$-independent manner when incubated in the presence of recombinant, constitutively active GST-mPAK3 (FIG. 2A). The force induced by GST-mPAK3 (~5 µg/ml; 55 nM) in relaxing buffer pCa <8.0) reached a maximum level equivalent to 62±12% (n=10) of that achieved by addition of a calcium-containing activation solution (pCa 4.3). Under the same conditions, a kinase-dead PAK mutant, GST-mPAK$^{K297R}$, was unable to induce force in the absence of $Ca^{2+}$ (FIG. 2B). In previous studies, $Ca^{2+}$-independent smooth muscle contraction has been induced through the use of unregulated forms of MLCK (Somlyo, A. P. et al, 1994. *Nature* 372:231–236; Stull, J. T. et al. 1991. *Hypertension* 17:723–732), addition of phosphatase inhibitors (e.g., Strauss, J. D. et al. 1992. *Am. J. Physiol.* 262:C1437–C1445; Paul, R. J. et al. 1987. *Prog. Clin. and Bio. Res.* 245:319–332; Trinkle-Mulcahy, L. et al. 1995. *J. Biol. Chem.* 270:18191–18194) or most recently by another Rho-Family GTPase-dependent kinase, ROK (Kurcishi, Y. et al. 1997. *J. Biol. Chem.* 272:12257–12260). In all cases the degree of smooth muscle contraction correlates with an increase in the level of $LC_{20}$ phosphorylation. In the case of ROK, contraction is promoted by the direct phosphorylation of $LC_{20}$ on serine 19 (Amano M, et al. 1996. *J. Biol. Chem.* 271:20246–20249) in addition to the phosphorylation and inhibition of myosin light chain phosphatase (MLCP) (Kimura, K., et al. 1996. *Science* 273:245–248).

Figure 2C:
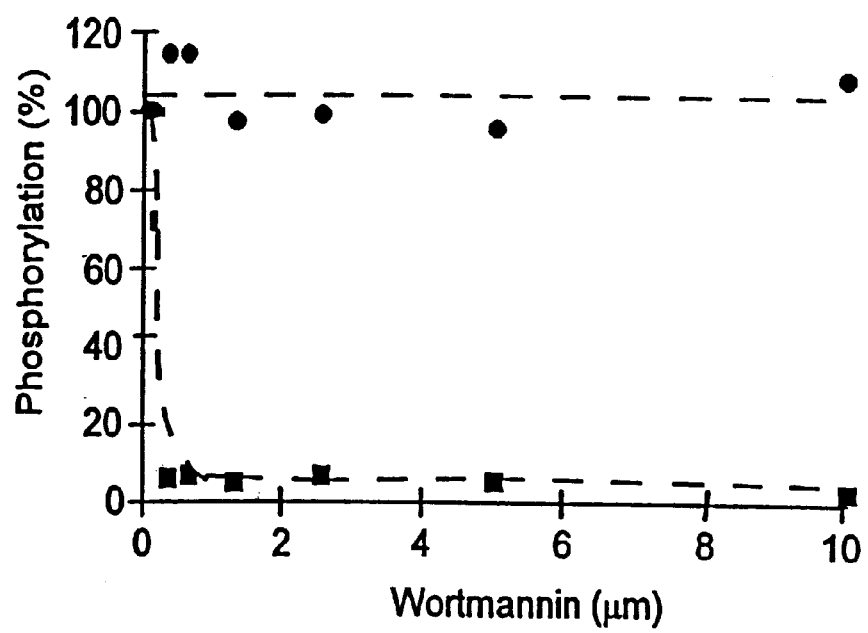
FIG. 2C shows the high specificity of wortmannin for MLCK by its ability to inhibit in vitro phosphorylation of $LC_{20}$ by MLCK (■) without inhibiting phosphorylation by GST-mPAK3 (●). 100% equals maximum phosphorylation of $LC_{20}$ (1 mole of phosphate per mole of protein) by either kinase in the absence of wortmannin.
Figure 2D:
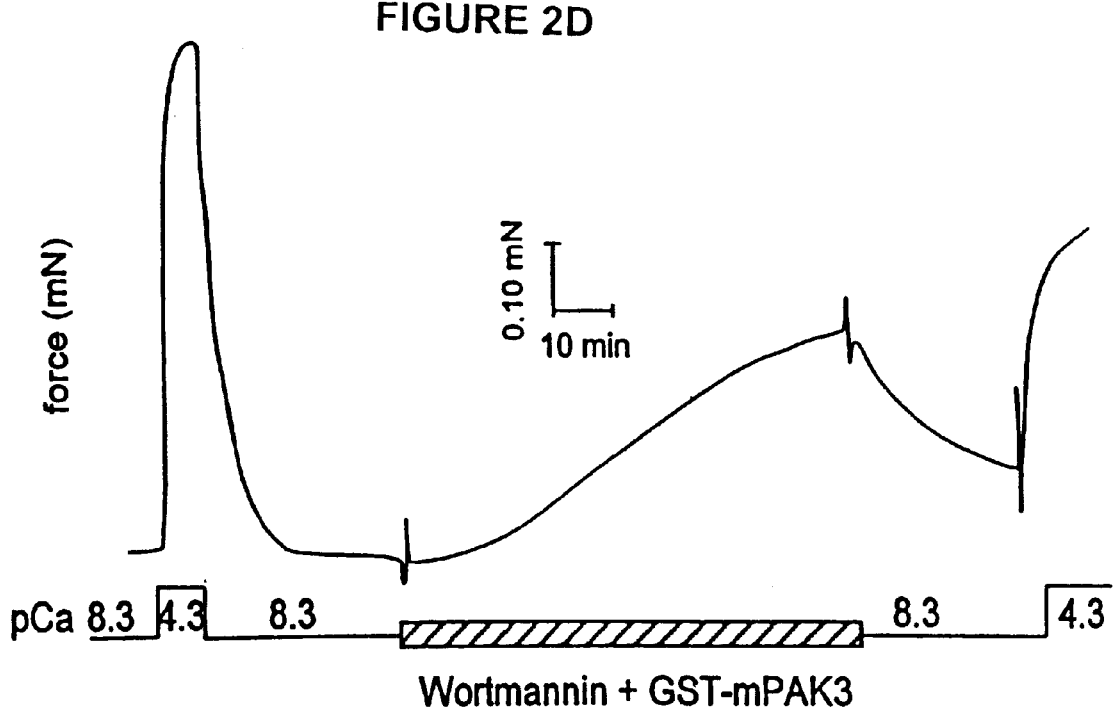
FIG. 2D shows a typical isometric force tracing of Triton X-100 skinned muscle fibers in the presence of 1 mM wortnainin and constitutively active GST-mPAK3. 1 mM wortmannin was sufficient to eliminate any $Ca^{2+}$-dependent contraction (data not shown), and would inhibit any contribution of MLCK to the contraction induced by the presence of PAK.
Figure 3A:
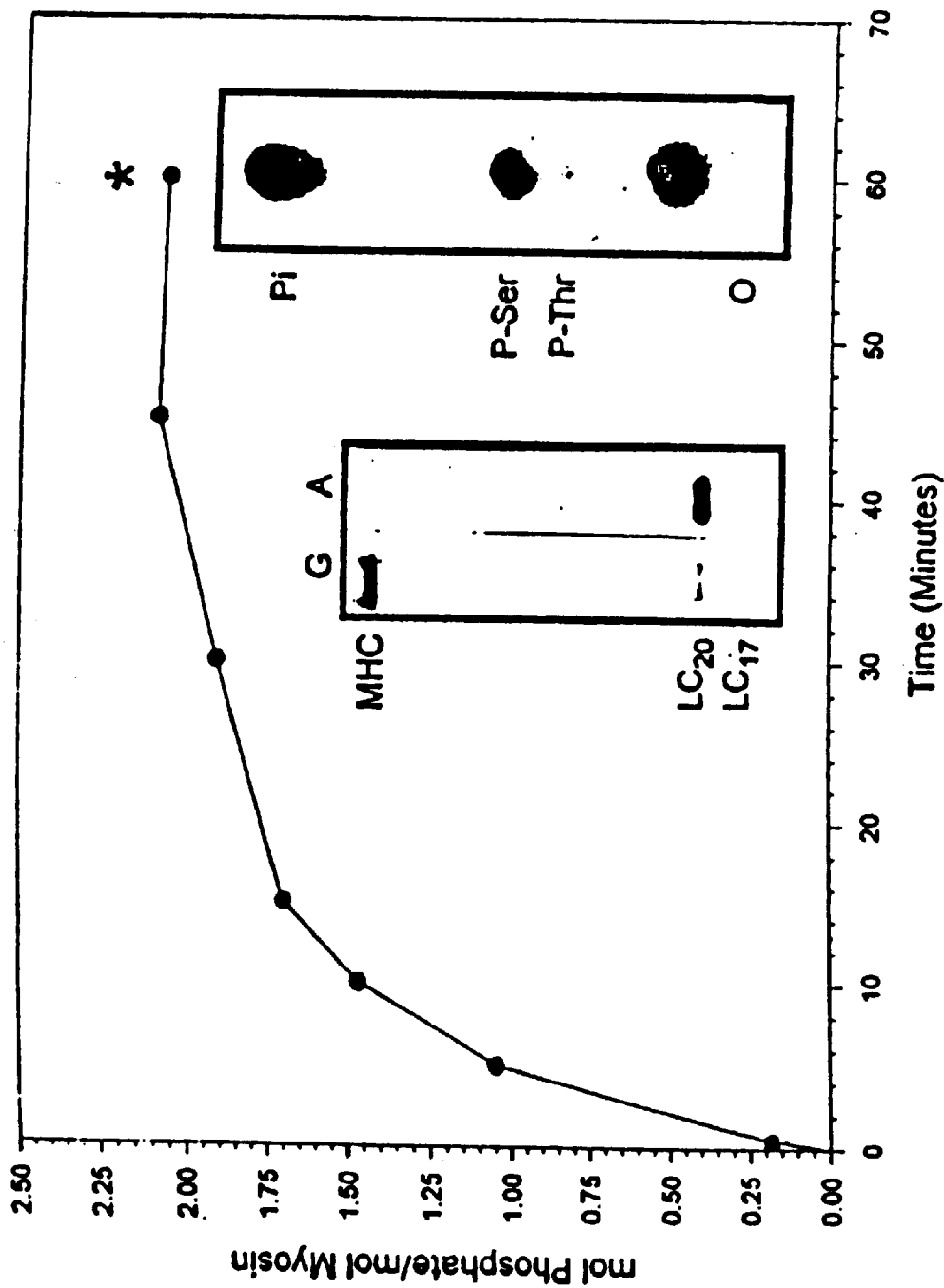
FIG. 3A shows the time course of in vitro phosphorylation of intact isolated chicken gizzard smooth muscle myosin by GST-mPAK3 (* Indicates time at which SDS-PAGE and autoradiography samples were obtained). Isolated smooth muscle myosin phosphorylated in vitro by GST-mPAK3 was analyzed by autoradiography of a 12.5% SDS-polyacrylamide gel (left inset; G=Coomassie stained gel, A=corresponding autoradiograph) and phospho-amino acid analysis (right inset).
Figure 3:
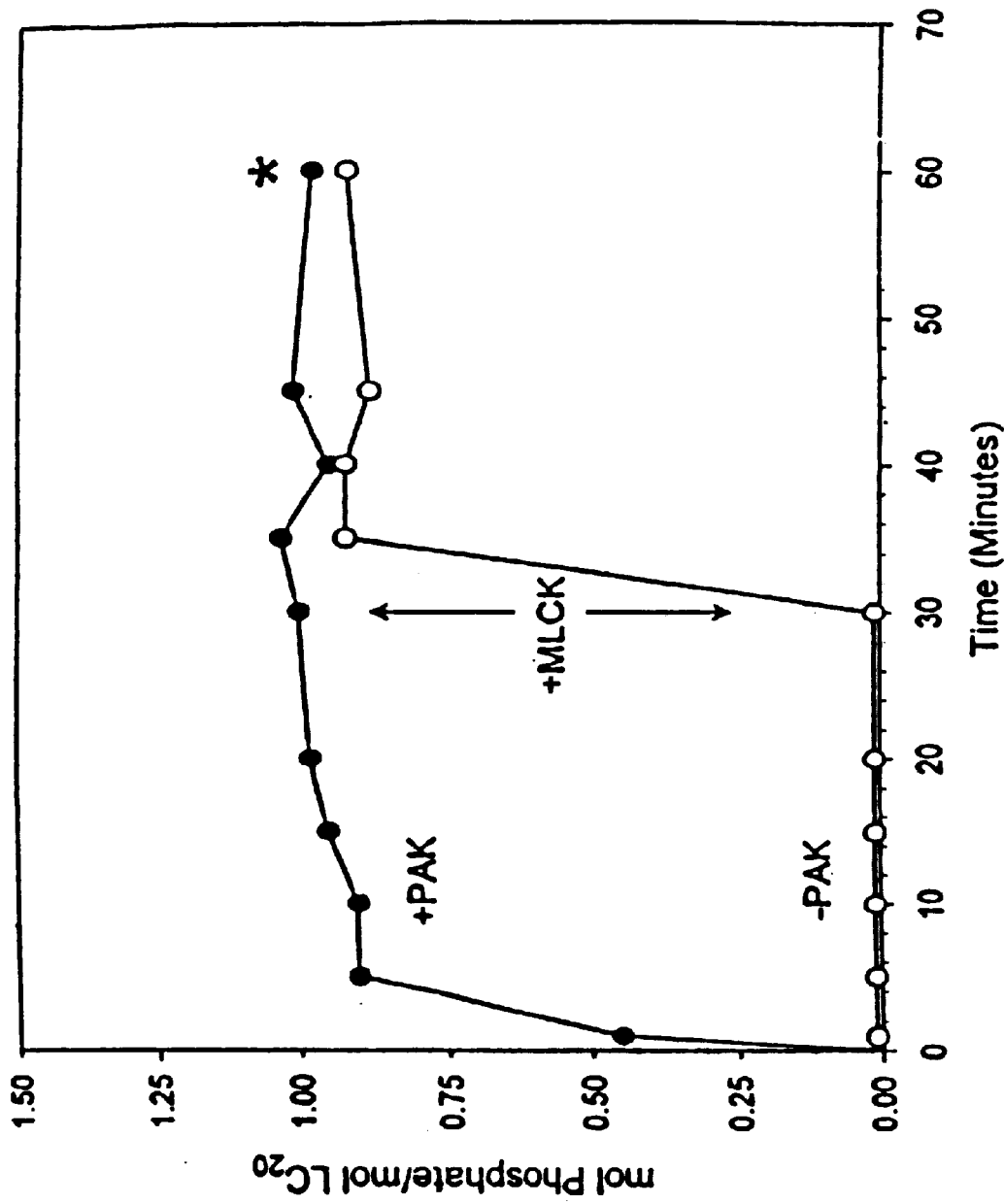
FIG. 3 shows uncoupling between $LC_{20}$ phosphorylation and force development in skinned muscle fibers even though isolated myosin and $LC_{20}$ can be phosphorylated at serine 19 by GST-mPAK3.
Figure 3C:
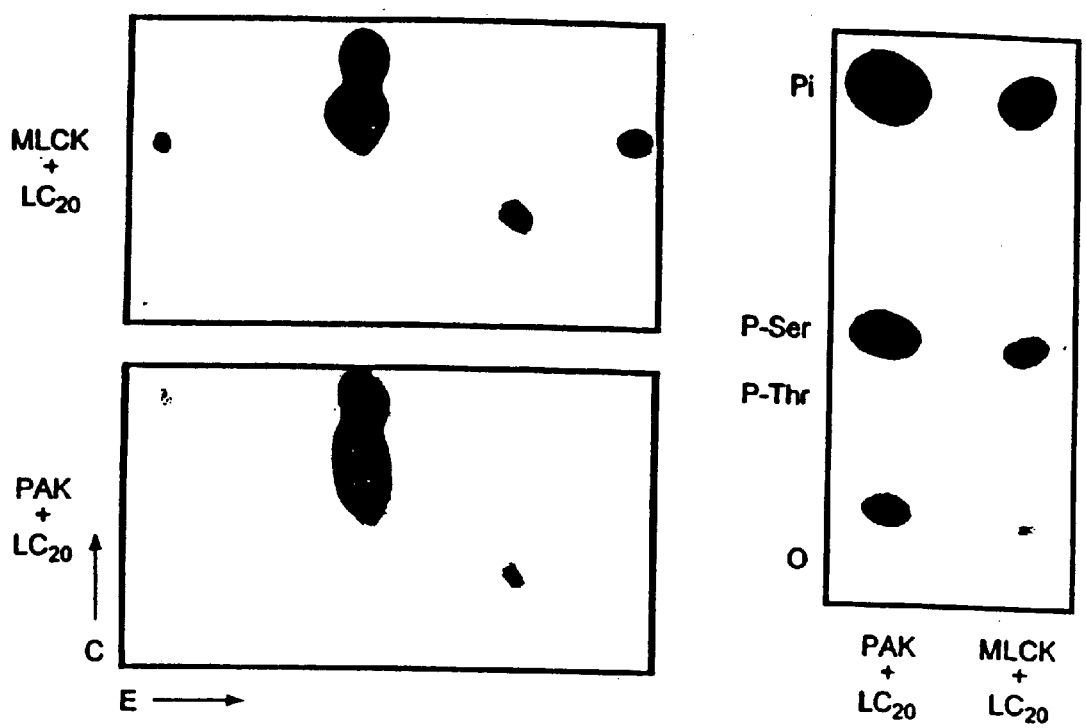
FIG. 3C shows typtic peptide maps (left insets) and phospho-amino acid analysis (right inset) of isolated smooth muscle $LC_{20}$ phosphorylated by MLCK or GST-mPAK3.
Figure 3:
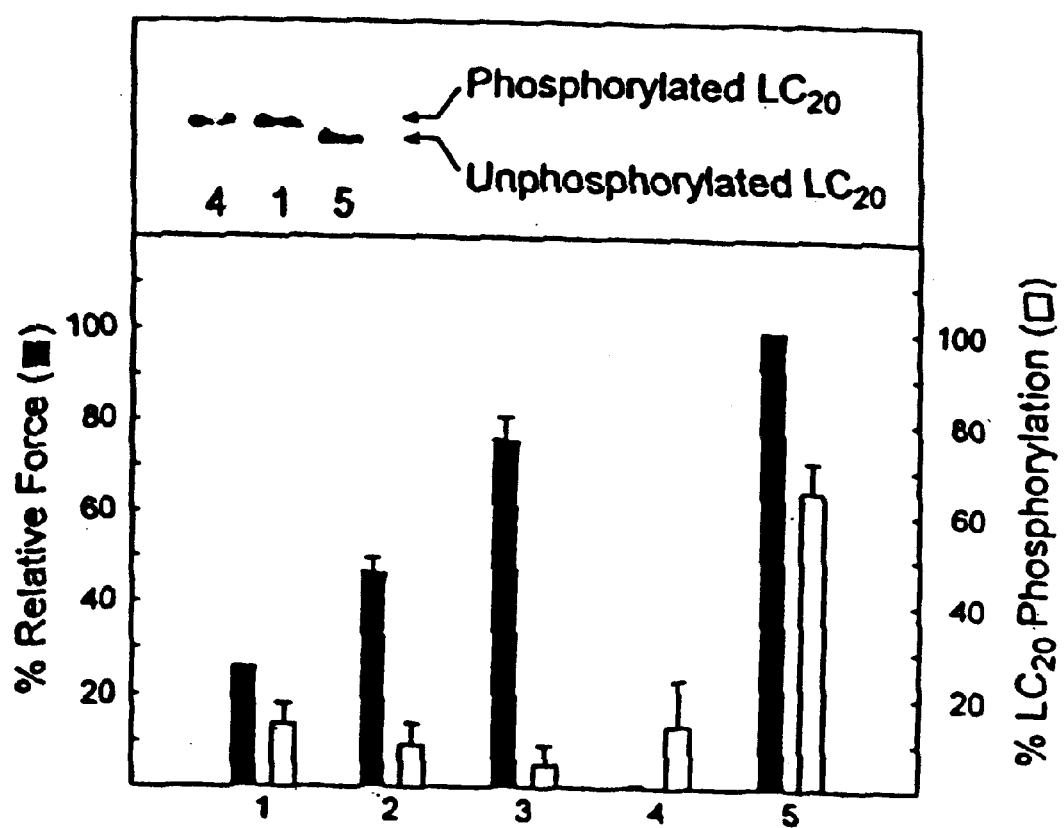

This dual effect of ROK was demonstrated by the use of wortmannin which is a potent inhibitor of MLCK but does not affect the activity of either ROK (Kureishi, Y. et al. 1997. *J. Biol. Chem.* 272:12257–12260) or PAK (FIG. 2C). The addition of a constitutively active GST-ROK catalytic domain to Triton-skinned smooth muscle fibers produces a wortmannin-sensitive contraction at pCa 6.5 ($Ca^{2+}$-dependent contraction) as well as a wortmannin-insensitive contraction at pCa <8.0 ($Ca^{2+}$-independent contraction) (Kureishi, Y. et al. 1997. *J. Biol. Chem.* 272:12257–12260). On the other hand, wortmannin at a concentration of 1 mM had little effect on the contraction of smooth muscle induced by GST-mPAK3 at low calcium (FIG. 2D), even though this concentration is sufficient to completely inhibit MLCK-dependent contraction at elevated $Ca^{2+}$ (data not shown). These results demonstrate that the $Ca^{2+}$-independent contraction promoted by PAK occurs without a requirement for MLCK activity. Furthermore, it seems unlikely that PAK promotes contraction by ihibiting myosin light chain phosphatase (MLCP) since the $Ca^{2+}$-independent contractions achieved with phosphatase inhibitors ame invariably dependent on MLCK activity and are abolished by MLCK inhibitors (e.g., Strauss, J. D. et al. 1992. *Am. J. Physiol.* 262:C1437–C1445; Paul, R. J. et al. 1987. *Prog Clin and Bio Res.* 245:319–332; Trinkle-Mulcahy, L. et al. 1995, *J. Biol. Chem.* 270:18191–18194). Thus, PAK most likely works by direct phosphorylation of a contractile protein rather then altering either MLCK or These results prompted an investigation into whether PAK directly phosphorylates $LC_{20}$ and thus achieves contraction in a "traditional" manner. In vitro analysis shows that GST-mPAK3 phosphorylates intact chicken gizzard smooth muscle myosin to 2 moles of phosphate per mmole (FIG. 3A). Phosphate is incorporated only into a single serine residue of $LC_{20}$ (FIG. 3A). Furthermore, MLCK was unable to phosphorylate $LC_{20}$ following GST-mPAK3 treatment (FIG. 3B), indicating that PAK and MLCK both phosphorylate serine 19. Indeed, identical two-dimensional typtic phosphopeptide maps were obtained from $LC_{20}$ phosphorylated by either MLCK or GST-mPAK3 (FIG. 3C). These results predict that PAK, like MLCK and ROK, promotes smooth muscle force generation by increasing $LC_{20}$ phosphorylation levels. However, under conditions where GST-mPAK3 induced Triton-skinned smooth muscle fibers to contract with ~70% of the maximal force obtained in the presence of $Ca^{2+}$, no significant increase in the level of $LC_{20}$ phosphorylation was observed (FIG. 3D). In fact, the level $LC_{20}$ phosphorylation remained similar to the level of relaxed fibers (absence of GST-mPAK3 and calcium, FIG. 3D lane 4) even as force induced by GST-mPAK3 increased from 26 to 70% (FIG. 3D, lanes 1–3). The uncoupling between $LC_{20}$ phosphorylation and force generation implies that PAK does not direct or indirectly activate myosin, but must employ an alternative and novel mechanism to contract the skinned muscle fibers.

To begin to define the molecular basis of PAK-induced contraction, it is critical to identify the proteins phosphorylated by mPAK3 in the skinned smooth muscle fibers. Protein substrates for mPAK3 were labeled with $^{32}$P under conditions where GST-mPAK3 produces ~70% of maximal $Ca^{2+}$-dependent force (FIG. 4). Gel electrophoresis analysis of the proteins labelled during a PAK-induced contraction were then performed. Two proteins, with approximate molecular weights of 58 and 145 kDa, were more highly phosphorylated in the presence than the absence of GST-mPAK3 (FIGS. 4A & C, compare lanes 2 and 3). The 58 and 145 kDa proteins were identified by western blot analysis as desmin and caldesmon, respectively. Little if any, phosphorylation of $LC_{20}$ was detected in the fibers contracted by GST-mPAK3.

GST-ROK, the GST-fusion protein of the constitutively active catalytic domain of ROK (Kureishi, Y. et al. 1997. *J. Biol. Chem.* 272:12257–12260). caused Triton-skinned smooth muscle fibers to contract in a $Ca^{2+}$-independent maimer with up to 80% of maximal force (Kureishi, Y. et al. 1997. *J. Biol. Chem.* 272:12257–12260). Under these conditions, the major proteins phosphorylated in the skinned fibers by GST-ROK were $LC_{20}$, desmin and two proteins of greater than 158 kDa (FIGS. 4B & D). Clearly, neither of these high molecular weight proteins are caldesmon (FIG. 4D). One is most likely the catalytic domain of MLCP, which is known to be phosphorylated by ROK in vitro and has an approximate molecular weight of 158 kDa by SDS PAGE.

In a comparison of the protein substrates for ROK and PAK under conditions where GST-ROK and GST-mPAK3 induce similar amount of $Ca^{2+}$-independent force (79.5 vs 71.1%, respectively), GST-ROK incorporated more phosphate into $LC_{20}$ than did GST-mPAK3. Phosphorylation of $LC_{20}$ by GST-ROK in the absence of calcium is similar to that by MLCK at pCa 4.3 (compare FIG. 4B lanes 3 and 4). As well, GST-ROK did not phosphorylate caldesmon, which is the main substrate for GST-mPAK3 (compare FIG. 4C lane 2 and FIG. 4D lane 3). In vitro phosphorylation studies confirm that chicken gizzard h-caldesmon is a better substrate for GST-mPAK3 than for GST-ROK (FIG. 4E). GST-mPAK3 phosphorylated hCAD to 2 moles of phosphate per mole of protein. The C-terminal domain of fibroblast 1-caldesmon (corresponding to chicken gizzard caldesmon residues 458–756) is a substrate for GST-mPAK3 (FIG. 4F) but no phosphorylation of the N-terminal caldesmon domain was observed (data not shown). The C-terminus of caldesmon contains multiple binding sites for actin, tropomyosin and calmodulin.

Caldesmon inhibits the actin-activated $Mg^{2+}$-ATPase of myosin (review see Chalovich, J. M. 1992. *Pharmacol. Ther.* 55:95–148) and has been suggested to provide a basal resting inhibition of vascular tone. The force of contraction of Triton-skinned smooth muscle fibers increases upon the partial extraction of caldesmon (Malmqvist, U. et al. 1996. *Pfluger Archiv.* 432:241–247) or decreases due to competitive binding of a 20-kDa actin-binding fragment of caldesmon (Pfitzer, G. et al. 1993. *Proc. Natl. Acad. Sci.* 90:5904–5908). As well, a synthetic peptide of an actin binding region of caldesmon increases force of β-escin skinned arterial muscle fibers at low concentrations of $Ca^{2+}$ (atsuyama, H. et al. 1992. *J. Biol. Chem.* 267:14555–14558), probably by competing with endogenous caldesmon for the actin filament. This could potentially revive caldesmon inhibition. This knowledge, taken together with the results of the present studies, led to a further investigation of whether a reduction in caldesmon interaction with actin would increase force generation resulting in contraction. Thus, the binding assay study described above investigated the affinity of unphosphorylated and PAK-phosphorylated caldesmon for the actin thin filament. The results, shown in FIG. 5, translate to an approximately two-fold reduction in the affinity of caldesmon for actin in the unphosphomylated and phosphorylated states. The data indicate that the mechanism of caldesmon inhibition of contraction is not related to the displacement of caldesmon from the actin thin filament, but probably a subtle movement of caldesmon on the actin filament.

Even with a small change in actin binding affinity, phosphorylation of caldesmon by PAK has a large effect on caldesmon function. As shown in FIG. 6, smooth muscle myosin ATPase activity was inhibited when caldesmon was unphosphorylated, whereas inhibition was clearly released in the presence of PAK-phosphorylated caldessnon. Thus, there is an increase in interaction between actin and myosin resulting in increased ATPase activity. Increased ATPase activity is positively correlated with increased force.

A possible PAK pathway responsible for contraction is shown schematically in FIG. 7.

Cardiac Muscle

Studies first investigated the presence of PAK in cardiac muscle. In a gel overlay assay, $GTP\gamma^{35}S$-Cdc42 bound to a 62kDa protein in porcine, dog, and rat cardiac muscle. As shown in FIG. 8, this protein comigrated with brain purified PAK and the PAK homologue form smooth muscle. The presence of PAK or a PAK homologue in cardiac muscle was thus confirmed.

The phosphorylation of cardiac muscle proteins by PAK and ROK was investigated using isolated cardiac myofibrils and associated proteins. PAK was inefficient at phosphorylating $LC_{20}$ when associated with isolated cardiac and skeletal myosin in the presence of, and hence while phosphorylating, myosin from smooth muscle and platelets (FIG. 9A). In contrast, ROK phosphorylated $LC_{20}$ in all of the various myosins tested (FIG. 9C). ROK phosphorylated cardiac $LC_{20}$ up to 0.5 mol phosphate per mol protein, and was equally effective at phosphorylating $LC_{20}$ as part of the myofibrils (FIG. 10) or as an isolated protein FIG. 9C).

Figure 12:
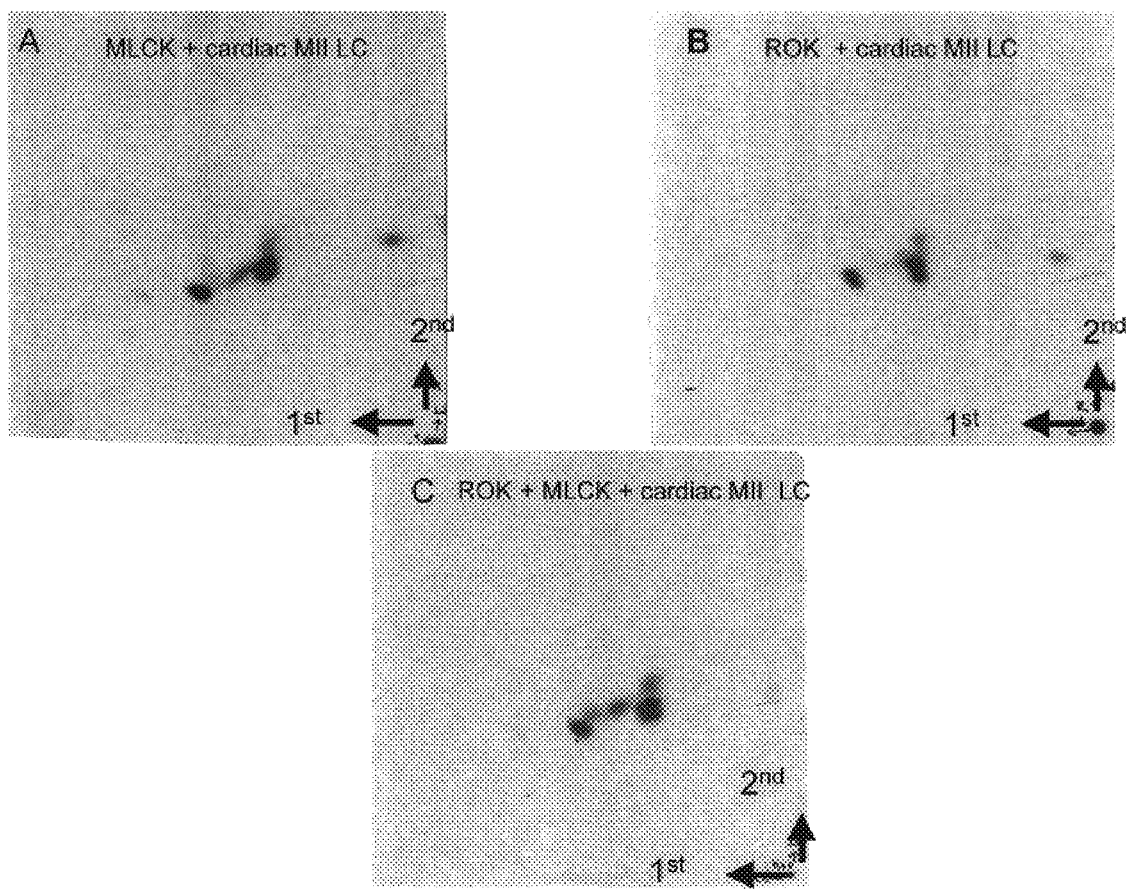

Smooth muscle MNCK, a kinase that specifically phosphorylates $LC_{20}$ resulting in smooth muscle contraction, also phosphorylated cardiac $LC_{20}$ (FIG. 9B), but at a low level of 0.2 mol phosphate per mol protein. The addition of both ROK and MLCK did not increase the level of phosphorylation of cardiac $LC_{20}$, indicating that the two kinases phosphorylate the same amino acid. This is supported by the fact that it is the same serine of cardiac $LC_{20}$ that is phosphorylated by either kinase (serine 16; FIG. 11), and the resulting phosphorylated cardiac $LC_{20}$s produce the same tryptic peptide map (FIG. 12).

Skeletal and cardiac muscle is regulated by the troponin (Tn) complex which is composed of TnI, TnT, and TnC. In the absence of calcium, TnI binds to actin and inhibits the actin-myosin interaction, resulting in relaxation. In the presence of calcium, TnI binds to TnC resulting in contraction. PAK is able to phosphorylate cardiac, but not skeletal Tn, and the autoradiograph of FIG. 13 indicates that TnI is the predominant troponin phosphorylated by PAK in the cardiac Tn complex.

Triton X-100 skinned cardiac muscle fibers were bathed in GST-mPAK in the absence (pCa 8.5) and presence of calcium at maximum (pCa 4.5) as well as at submaximal calcium concentrations. As shown in FIG. 14A, PAK had no effect in the absence of calcium and little effect ( 3%) at maximum concentration in the force developed by the skinned fibers. However, PAK caused up to a 174% (range, 25.6 to 441.7%, n=4) increase in force at submaximal calcium concentration (pCa 6.25), and at pCa 5.5, the average increase in force was 105% (range, 25.7 to 185.7%, n=4)(FIG. 14B). A representative trace of skinned cardiac muscle fiber contraction is shown in FIG. 15.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying an agent that modulates the kinase activity of a PAK protein (p21 activated kinase), comprising:

providing an indicator composition comprising a PAK protein having PAK kinase activity, wherein the indicator composition includes a member of the group consisting of a smooth muscle cell extract, a detergent-skinned smooth muscle fiber bundle system, a cardiac muscle cell extract, and a detergent-skinned cardiac muscle fiber bundle system;

contacting the indicator composition with a test agent; and determining an effect of the test agent on PAK kinase activity in the indicator composition to thereby identify a compound that modulates the kinase activity of a PAK protein.

2. The method of claim 1, wherein PAK kinase activity is assessed by measuring phosphorylation of caldesmon or a fragment thereof.

3. The method of claim 1, wherein PAK kinase activity is assessed by measuring phosphorylation of calponin or a fragment thereof.

4. The method of claim 1, wherein PAK kinase activity is assessed by measuring phosphorylation of troponin I (TnI) or a fragment thereof.

5. The method of claim 1, wherein PAK kinase activity is assessed by measuring phosphorylation of desmin or a fragment thereof.

6. The method of claim 1, wherein the identified compound changes the calcium sensitivity of smooth or cardiac muscle.

7. The method of claim 1, wherein degree of $Ca^{2+}$-independent contraction in the presence and absence of the test agent is determined.

8. The method of claim 1, wherein degree of $Ca^{2+}$-dependent contraction in the presence and absence of the test agent is determined.

* * * * *